United States Patent
Tonelli et al.

(10) Patent No.: US 7,223,336 B2
(45) Date of Patent: *May 29, 2007

(54) INTEGRATED BLOOD TREATMENT MODULE AND EXTRACORPOREAL BLOOD TREATMENT APPARATUS

(75) Inventors: Claudio Tonelli, Modena (IT); Vincenzo Baraldi, Quistello (IT); Massimo Zaccarelli, San Felice Sul Panaro (IT); Annalisa Delnevo, Sant'Agata Bolognese (IT); Francesco Ribolzi, Modena (IT); Jacques Chevallet, Serezin du Rhone (FR); Jacques Duchamp, Bron (FR); Aziz Aberkane, Decines (FR); Gabriel Meyssonnier, Dizimieu (FR); Dominique Pouchoulin, Tramoyes (FR)

(73) Assignee: Gambro Lundia AB, Lund (SE)

( * ) Notice: Subject to any disclaimer, the term of this patent is extended or adjusted under 35 U.S.C. 154(b) by 399 days.

This patent is subject to a terminal disclaimer.

(21) Appl. No.: 10/771,427

(22) Filed: Feb. 5, 2004

(65) Prior Publication Data

US 2004/0158189 A1    Aug. 12, 2004

Related U.S. Application Data

(60) Provisional application No. 60/470,452, filed on May 15, 2003.

(30) Foreign Application Priority Data

Feb. 7, 2003   (IT)   .......................... MI2003A0211

(51) Int. Cl.
*B01D 61/00* (2006.01)
*A61M 1/00* (2006.01)
*A61M 37/00* (2006.01)

(52) U.S. Cl. .................. 210/232; 210/239; 210/240; 210/258; 210/416.1; 604/6.09; 604/6.11

(58) Field of Classification Search ................ 210/232, 210/239, 240, 258, 321.6, 416.1, 249; 604/6.09, 604/6.11; 137/111, 269; 138/111, 115, 118
See application file for complete search history.

(56) References Cited

U.S. PATENT DOCUMENTS 3,909,045 A    9/1975   Meagher ...................... 285/22

(Continued)

FOREIGN PATENT DOCUMENTS

AU          744404          1/1999

(Continued)

OTHER PUBLICATIONS

International Search Report for International Application No. PCT/IB2004/000104.
English language abstract of EP 0 877 100 A1, Thomson Derwent.

(Continued)

*Primary Examiner*—John Kim
(74) *Attorney, Agent, or Firm*—Finnegan, Henderson, Farabow, Garrett & Dunner, L.L.P.

(57) ABSTRACT

The invention relates to an integrated blood treatment module (1) comprising a support element (4) and a fluid distribution circuitry associated thereto; the distribution circuitry comprises at least a blood line (44), a portion of which is secured to the support element and defines with the latter at least a U-shaped tube length (44*a*) designed to cooperate, when in use, with a respective pump (3*a*). There are then further fluid lines (45, 48, 50, 51) fastened to the support element and defining each at least a U-shaped tube length (45*a*, 48*a*, 50*a*, 51*a*) with respect to said element and each designed to cooperate, when in use, with a respective pump (3*b*, 3*c*, 3*d*, 3*e*). The support element has a first zone (274) in which the portion of the blood line is secured, and at least a second zone (275) opposite said first zone, to which all the corresponding further tube lengths are fastened.

33 Claims, 19 Drawing Sheets

U.S. PATENT DOCUMENTS

| | | | |
|---|---|---|---|
| 4,009,107 A | 2/1977 | Miller et al. | 210/321 B |
| 4,263,808 A | 4/1981 | Bellotti et al. | 73/714 |
| 4,379,452 A | 4/1983 | DeVries | 604/6 |
| 4,424,009 A | 1/1984 | van Os | 417/394 |
| 4,436,620 A | 3/1984 | Bellotti et al. | 210/90 |
| 4,526,515 A | 7/1985 | DeVries | 417/63 |
| 4,637,813 A | 1/1987 | DeVries | 604/6 |
| 4,844,810 A | 7/1989 | Richalley et al. | |
| 4,871,012 A | 10/1989 | Kuo | 165/41 |
| 4,886,431 A | 12/1989 | Soderquist et al. | 417/477 |
| 4,950,245 A | 8/1990 | Brown et al. | 604/153 |
| 5,311,908 A | 5/1994 | Barone et al. | |
| 5,427,509 A | 6/1995 | Chapman et al. | 417/477.2 |
| 5,441,636 A * | 8/1995 | Chevallet et al. | 210/232 |
| 5,462,416 A | 10/1995 | Dennehey et al. | 417/477.2 |
| 5,482,440 A | 1/1996 | Dennehey et al. | 417/63 |
| 5,641,144 A | 6/1997 | Hendrickson et al. | 248/292.13 |
| 5,714,060 A | 2/1998 | Kenley et al. | 210/194 |
| 5,919,154 A * | 7/1999 | Toavs et al. | 604/4.01 |
| 5,983,947 A | 11/1999 | Utterberg | 138/89 |
| 6,277,277 B1 | 8/2001 | Jacobi et al. | 210/240 |
| 6,280,406 B1 * | 8/2001 | Dolecek et al. | 604/4.01 |
| 6,308,721 B1 | 10/2001 | Bock et al. | 134/166 R |
| 6,325,775 B1 | 12/2001 | Thom et al. | 604/6.02 |

FOREIGN PATENT DOCUMENTS

| | | |
|---|---|---|
| AU | 199870078 A1 | 1/1999 |
| AU | 199870078 B2 | 1/1999 |
| EP | 0 134 436 B1 | 1/1988 |
| EP | 0 256 956 B1 | 2/1988 |
| EP | 0 116 596 B1 | 11/1990 |
| EP | 0 282 539 B1 | 1/1992 |
| EP | 0 611 227 A1 | 8/1994 |
| EP | 0 643 808 B1 | 1/1998 |
| EP | 0 695 397 B1 | 9/1998 |
| EP | 0 887 100 A1 | 12/1998 |
| EP | 0 893 603 A2 | 1/1999 |
| EP | 0 694 125 B1 | 2/1999 |
| EP | 0 686 237 B1 | 5/1999 |
| EP | 0 992 256 A2 | 4/2000 |
| EP | 0 679 099 B1 | 7/2001 |
| EP | 0 852 953 B1 | 11/2001 |
| GB | 2 076 476 A | 12/1981 |
| GB | 2 110 564 | 6/1983 |
| GB | 2 208 896 A | 4/1989 |
| WO | WO 88/01895 | 3/1988 |
| WO | WO 95/17597 | 6/1995 |
| WO | WO 95/17598 | 6/1995 |
| WO | WO 95/17599 | 6/1995 |
| WO | WO 95/17600 | 6/1995 |
| WO | WO 95/17601 | 6/1995 |
| WO | WO 95/17602 | 6/1995 |
| WO | WO 95/17603 | 6/1995 |
| WO | WO 95/17604 | 6/1995 |
| WO | WO 97/02056 | 1/1997 |
| WO | WO 97/10436 | 3/1997 |
| WO | WO 98/22163 | 5/1998 |
| WO | WO 99/13926 | 3/1999 |
| WO | WO 01/08722 | 2/2001 |
| WO | WO 01/08772 A2 | 2/2001 |
| WO | WO 02/26288 A2 | 4/2002 |

* cited by examiner

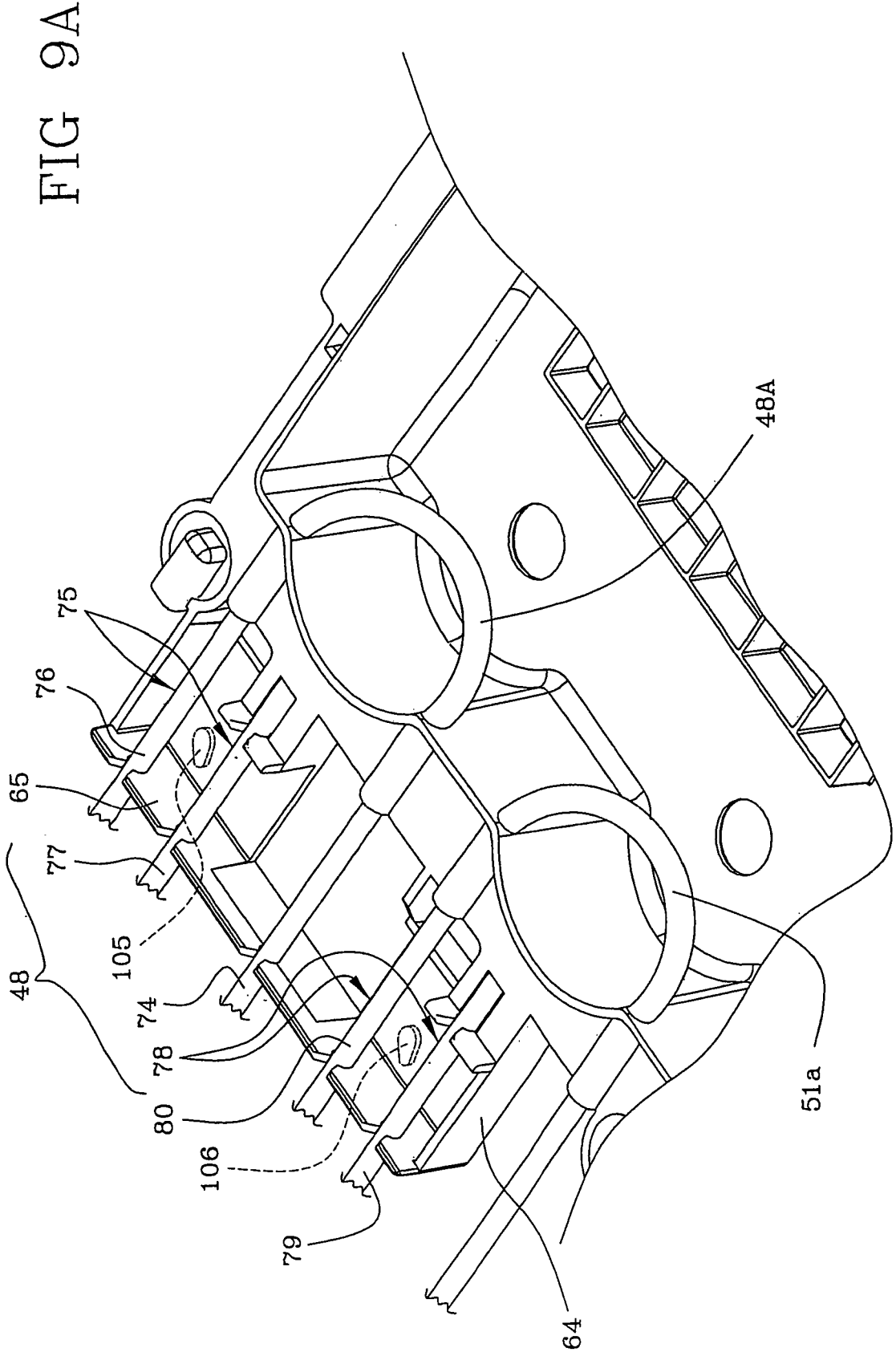

INTEGRATED BLOOD TREATMENT MODULE AND EXTRACORPOREAL BLOOD TREATMENT APPARATUS

CROSS REFERENCE TO RELATED APPLICATIONS

This application claims the priority of Italian Patent Application No. MI2003 A 000211, filed on Feb. 7, 2003, and the benefit of U.S. Provisional Application No. 60/470,452, filed May 15, 2003, the contents of which are incorporated herein by reference.

BACKGROUND OF THE INVENTION

The present invention relates to an integrated blood treatment module and to an extracorporeal blood treatment apparatus that can receive said integrated module.

As is known, in order to carry out extracorporeal blood treatments such as for instance haemodialysis, haemofiltration, haemodiafiltration, plasmapheresis, extracorporeal blood oxygenation, extracorporeal blood filtration or other treatments, it is necessary to provide for at least an extracorporeal circuit through which the blood flows and is conveyed towards a treatment unit; the treated blood is then carried back to the patient's cardiovascular system. Referring by way of example to a dialysis treatment, the extracorporeal circuit used comprises: a dialysis filter consisting of a housing body defining at least a first and a second chamber separated from each other by a semipermeable membrane, a blood intake line leading to the first chamber of the dialysis filter and a blood return line designed to receive blood coming out of the first chamber and to carry it back to the patient. The second chamber of the dialysis filter is then connected to a circuit for the circulation of a dialysis liquid designed to receive the impurities that are present in the blood and the excess fluid that has to be removed from the patient's blood.

Currently, in apparatus for extracorporeal blood treatments all the lines designed for the circulation of the dialysis liquid are housed within the dialysis apparatus, whereas the lines constituting the extracorporeal blood circuit are replaced at every treatment and suitably connected to the dialyzing filter, which can be replaced either at every treatment or from time to time, as required.

From a structural point of view the dialysis filter, the lines for the circulation of the dialyzing liquid and the lines constituting the intake branch carrying the blood back to the patient consist of separate parts that are connected and cooperate during operation after being suitably assembled.

There are also apparatus that are available on the market at present, designed in particular for intensive treatment of kidney failure, which are advantageously equipped with integrated modules comprising a support structure, a dialyzing filter engaged to the support structure by means of a suitable support projecting from said structure, as well as a hydraulic circuit comprising the tubes that are necessary to define the blood suction and return lines leading to the patient, the possible lines for the infusion of anticoagulant or substitution liquids, the intake line for the dialysis liquid and the discharge line for the liquid coming out of the second chamber of the dialyser.

The integrated modules described above enable an easy and immediate association of the lines to the treatment apparatus and do not require any connection between the treatment unit, such as for instance a dialysis filter, and the various tubes or lines designed to convey blood and other fluids. Moreover, said integrated modules enable the removal both of the tubes conveying the blood and of the tubes conveying other fluids at the end of the treatment. In other words, thanks to a simple loading and connecting operation of the terminals and of the fluid conveyance lines to the corresponding sources such as bags or others, the user can install a dialysis apparatus. Analogously, once the treatment step is over, by simply disconnecting and disassembling the integrated module from the blood treatment apparatus in few operations, the operator can completely eliminate both extracorporeal circuit and the blood treatment unit, as well as the tubes for the circulation of possible infusion liquids and of the dialysis liquid. The easy installation of said modules ensures an efficiency and a speed that are certainly advantageous for intensive treatments where the personnel, who might not be conversant with the use of blood treatment apparatuss, can thus operate rapidly and with a high reliability.

In particular, it is known about integrated modules for extracorporeal blood treatment in which a quadrangular plate, thanks to the use of an auxiliary engagement structure, centrally carries the blood treatment filter and also supports on each of its sides four tube lengths of corresponding lines of the fluid distribution circuitry.

In particular, each of the four sides has two connectors to which a respective tube length, basically semicircular, is secured; each length can be engaged by a respective peristaltic pump.

The four ring-shaped tube lengths extend away from the four sides and all have the same shape and size.

In particular, the part of the module consisting of the support plate and of the U-shaped tube lengths is symmetrical with respect to two orthogonal axes.

The arrangement referred to above, though being widely used today in integrated modules designed for intensive therapy apparatus, has proved to be susceptible of several improvements.

First of all, it should be noted that the particular relative arrangement of the various U-shaped tube lengths and, therefore, of the respective pumps supported by the apparatus do not allow to optimize the lengths of the various portions of tubes in which blood, dialysis fluids, waste fluids, etc.

Furthermore, it is not possible to use pumps with larger size (which would thus involve U-shaped tube lengths with larger size) in any of the lines without prejudicing the compactness and the overall dimensions of the integrated module.

Eventually, it should be noted that the module at the state of the art is necessarily designed for a maximum of four peristaltic pumps for conveying the respective fluids, since other infusion lines beyond those that are already provided cannot be installed.

SUMMARY OF THE INVENTION

The present invention therefore aims at solving basically the drawbacks and operating limitations referred to above.

A first aim of the invention is to carry out an integrated module in which the arrangement of the various tube lengths allows a high compactness of said module as well as an optimal distribution of the lengths of the various lines of the hydraulic circuit.

A further aim of the invention is to enable the presence of at least a blood line in which the biological fluid can be conveyed by pumps with larger radial size without damaging the compactness of said integrated module.

Finally, an auxiliary aim of the invention is to carry out an integrated module that can protect the various U-shaped tube lengths on which the peristaltic pumps act, thus protecting also the latter while the apparatus is working.

These and other aims, which shall be evident in the course of the present description, are basically achieved by an integrated module and by an apparatus as described in the appended claims.

Further characteristics and advantages will be clearer from the detailed description of a preferred though not exclusive embodiment of a support element, of an integrated module and of a corresponding apparatus for extracorporeal blood treatment according to the present invention.

BRIEF DESCRIPTION OF THE DRAWINGS

This description will be given below with reference to the appended drawings, which are provided as a mere guidance and are therefore not limiting, in which:

FIG. 9*a* shows an enlarged detail of the module of FIG. 9;

DETAILED DESCRIPTION

Figure 1:
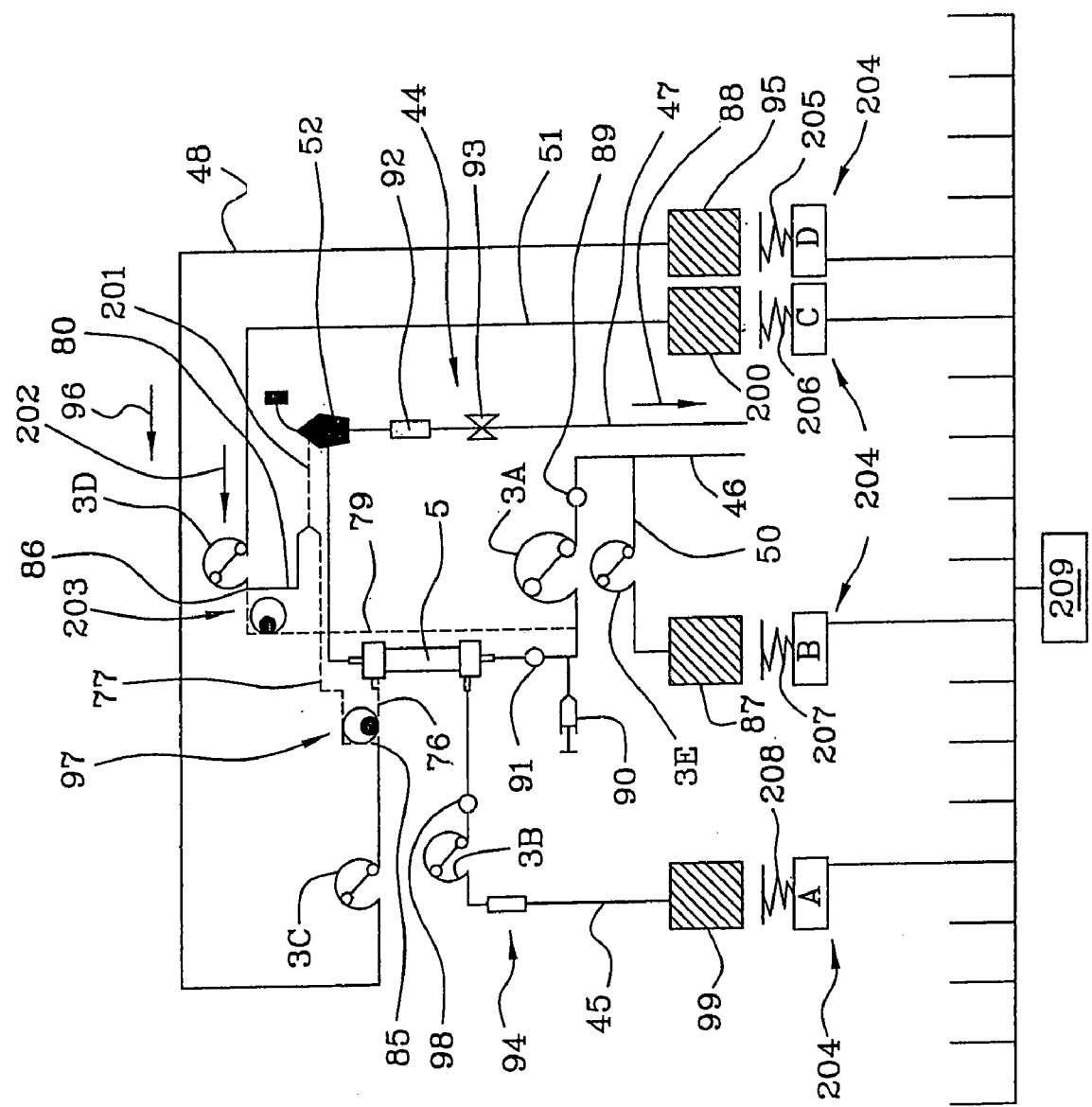
FIG. 1 shows a schematic view of a hydraulic circuit carried out by an apparatus and a module according to the present invention.

With reference to the figures mentioned above the numeral 4 globally refers to a support element according to the present invention.

Conversely, the numeral 1 refers to an integrated module (combination of a support element 4, a distribution circuitry 15 and a blood treatment unit 5) that can be used together with extracorporeal blood treatment apparatus 2 according to the present invention.

As can be inferred from the appended Table 1, the global hydraulic circuit carried out thanks to the cooperation between the integrated module and the apparatus consists of a blood line or circuit 44, which takes blood from a patient, for instance by means of a catheter introduced into a vein or artery of said patient, and through at least an intake branch or inlet line 46 carries said blood, for instance continuously, to a filtration unit 5.

Then the blood passes through a primary chamber of said filtration unit 5 and through an outlet line 47 the treated blood is carried back to the patient.

The connection with an auxiliary pre-infusion line 50 is provided immediately downstream from the blood collecting zone on the inlet line 46.

In particular, the apparatus is equipped with at least a secondary fluid container or bag 87 for supplying the pre-infusion line 50; by using corresponding means for conveying fluid, in the example shown comprising an auxiliary pre-infusion pump 3*e*, for instance a peristaltic pump, it is possible to control the fluid flow within said line by introducing said fluid directly into the blood by means of a direct connection to the inlet line 46.

Generally, the secondary fluid container 87 can house a suitable biological fluid for a pre-infusion, however said bag 87 can also contain an anticoagulant, generally having such a topical nature as to ensure a particular working of the apparatus as shall be explained below in further detail.

After defining a direction of blood circulation 88 from the inlet line 46 towards the filtration unit and from the latter through the outlet line 47 towards the patient, a known blood pressure sensor 89, which shall not be described in further detail, is placed immediately downstream from the auxiliary pre-infusion line 50.

The blood circuit 44 therefore comprises means for conveying fluid, i.e. in this particular case at least a blood pump 3*a* for controlling and managing the suitable blood flow in the circuit.

Also the blood pump 3*a* is generally a peristaltic pump.

Following the direction of blood circulation 88, there is then a device 90 for administering an anticoagulant, for instance a syringe containing suitable doses of heparin.

The blood then passes through another pressure sensor 91 controlling the correct flow within the blood circuit.

After passing through a main chamber of the filtration unit 5, where the suitable exchanges of substances, molecules and fluids occur by means of a semipermeable membrane, the treated blood enters the outlet line 47 first passing through a gas separating device (generally air) 52 commonly known as "bubble trap", designed so as to ensure the removal of substances or air bubbles present in the blood or introduced into the blood during treatment.

The treated blood getting out of the separating device 52 then passes through an air bubble sensor 92 verifying the absence of said dangerous formations within the treated blood that has to be re-introduced in the patient's blood circulation.

Immediately downstream from the bubble sensor 92 there is an element 93 which, in case of alarm, can block the blood flow towards the patient.

In particular, should the bubble sensor 92 detect the presence of anomalies in the blood flow, the apparatus through the element 93 (be it a tap, a clamp or similar) would be able to block immediately the passage of blood so as to avoid any consequence to the patient.

Downstream from said element 93 the treated blood is then carried back to the patient undergoing therapy.

The extracorporeal blood treatment apparatus shown above is then equipped with a fluid circuit 94, which is also provided with at least an inlet line 48 leading into the filtration unit 5 and with an outlet line 45*b* from the filtration unit.

At least a primary fluid container 95 is designed to supply the inlet line 48 of the fluid circuit 94 (generally the primary fluid container 95 shall consist of a bag containing a suitable dialyzing liquid).

The inlet line 48 then comprises means for conveying fluid such as a least a pump 3*c* (in the embodiment shown a peristaltic pump) for controlling the flow of liquid from the bag 95 and for defining a direction of circulation 96.

Downstream from the pump 3*c* in the direction of circulation 96 there is a branching 85 splitting the fluid circuit 94 up into an intake branch 76 and into an infusion branch 77.

In particular, the infusion branch 77 is connected to the outlet line 47 of the blood circuit 44.

In other words, by means of said infusion branch 77 it is possible to obtain a post-infusion directly in the blood line using the content of the primary fluid container 95.

Conversely, the intake branch 76 conveys the fluid directly to the filtration unit and in particular to a secondary chamber of said unit.

The fluid circuit 94 is further equipped with selecting means 97 for determining the percentages of fluid flow within the infusion branch 77 and the intake branch 76.

Generally said selecting means 97, usually placed near the branching 85, can be positioned at least between a first operating condition in which they allow the passage of fluid in the intake branch 76 and block the passage in the infusion branch 77, and a second operating condition in which they allow the passage of fluid in the infusion branch 77 and block the passage in the intake branch 76.

In other words, said selecting means 97 can consist of a valve element operating on the fluid circuit 94 by alternatively blocking the passage of fluid in either branch.

It is also evident that it might be provided for suitable selectors, which are able to establish a priori the amount of liquid that has to pass through both branches simultaneously.

It will also be possible to vary the percentages of fluid in either branch as a function of time and of the preestablished therapies.

The dialyzing liquid through the intake branch 76 gets into a secondary chamber of the filtration unit 5.

In particular, the primary chamber through which the blood flow passes is separated from the secondary chamber through which the dialyzing liquid passes by means of a semipermeable membrane ensuring the suitable passage of the dangerous substances/molecules and of fluid from the blood towards the dialyzing liquid mainly by means of convection and diffusion processes, and also ensuring through the same principles the passage of substances/molecules from the dialyzing liquid towards the blood.

The dialysis fluid then gets into the outlet line 45 and passes through a suitable pressure sensor 98 whose function is to control the working of said line.

Then there are means for conveying fluid, for instance a suction pump 3*b* controlling the flow in the outlet line 45 within the fluid circuit 94.

Also said pump will generally be a peristaltic pump.

The fluid to be eliminated then passes through a blood detector and is conveyed into a collection container or bag 99.

Further analyzing the peculiar circuit of the apparatus according to the invention, note the presence of at least another infusion line 51 acting on the outlet line 47 of the blood circuit 44.

In particular, the infusion fluid is taken from at least an auxiliary container 200 and is sent directly to the outlet line 47 of the blood circuit 44 through means for conveying fluid, generally an infusion pump 3*d* controlling its flow (in the example a peristaltic pump).

In particular and as can be observed in the appended figure, the infusion liquid can be introduced directly into the gas separating device 52.

As can also be inferred, the infusion branch 77 of the fluid circuit 94 and the infusion line 51 are equipped with a common end length 201 letting into the blood circuit 44.

Said intake end length 201 is placed downstream from the infusion pump 3*d* with respect to a direction of infusion 202 and carries the fluid directly into the bubble trap device 52.

Further referring to the diagram in FIG. 1, note the presence within the infusion line 51 of at least a pre-infusion branch 79 connected to the inlet line 46 of the blood circuit 44.

In further detail, downstream from the infusion pump 3*d* with respect to the direction of infusion 202, there is a branching 86 splitting the infusion line 51 up into pre-infusion branch 79 and post-infusion branch 80.

The pre-infusion branch 79, in particular, carries the fluid taken from the bag 200 on the inlet line 46 of the blood circuit downstream from the blood pump 3*a* with respect to the direction of circulation 88.

Conversely, the post-infusion branch 80 is connected directly to the common end length 201.

The infusion line 51 further comprises selecting means 203 for determining the percentage of liquid flow to be sent to the post-infusion branch 80 and to the pre-infusion branch 79.

The selecting means 203 placed near the branching 86 can be positioned between at least a first operating condition in which they allow the passage of fluid in the pre-infusion branch 79 and block the passage in the post-infusion branch 80, and at least a second operating condition in which they allow the passage of fluid in the post-infusion branch 80 and block the passage in the pre-infusion branch 79.

Obviously, as in the case of the selecting means 97 present on the fluid circuit 94, also the other selecting means 203 will be able to determine the percentage of fluid that has to pass in each of the two branches and to possibly vary it in time in accordance with the planned therapies. Moreover, the selecting means 97 and the other selecting means 203 will generally though not necessarily be of the same nature.

The apparatus is then equipped with means 204 for determining at least the weight of the primary fluid container 95 and/or of the auxiliary fluid container 200 and/or of the secondary fluid container 87 and/or of the collection container 99.

In particular, said means 204 comprise weight sensors, for instance respective scales 205, 206, 207, 208 (at least an independent one for each fluid bag associated to the apparatus).

In particular, there will be at least 4 of said scales, each pair being independent from the other and measuring the respective weight of a bag.

It should then be pointed out that there is a processing unit or CPU 209 acting on the blood circuit 44 and in particular on the pressure sensor 89, on the blood pump 3a, on the device 90 for heparin infusion, on the other pressure sensor 91, and on the device for detecting the presence of air bubbles 92 and on its respective closing element 93.

Said CPU 209 has also to control the fluid circuit 94 and, in particular, shall be input with the data detected by the scales 205 and concerning the weight of the bag 95 and shall act on the pump 3c, on the selecting means 97, on the pressure sensor 98, then on the suction pump 3b and shall eventually receive the data detected by the scales 208 whose function is to determine the weight of the collection container 99.

The CPU 209 shall also act on the infusion line 51 checking the weight of the auxiliary container 200 (checked by the scales 206) and will be able to control both the infusion pump 3d and the other selecting means 203.

Eventually, the CPU 209 shall also act on the auxiliary pre-infusion line 50 detecting the weight of the secondary fluid container 87 by means of the scales 207 and suitably controlling the pump 3e according to the treatments to be carried out.

Reminding that the above description has been made with the sole purpose of describing the whole of the hydraulic circuit of the extracorporeal blood treatment apparatus, here is a short description of the working of the device.

Once the whole hydraulic circuit and the filtering unit 5 have been correctly associated to the apparatus so that the various peristaltic pumps engage the respective lengths of tubes and that all the sensors have been suitably positioned, and the various bags containing the various fluids have been associated to the corresponding liquid intake/suction lines, and the blood circuit has been connected to a patient's artery/vein, the initial circulation of blood within its circuit is enabled.

Therefore, according to the kind of therapy that has been set, the extracorporeal blood treatment apparatus is automatically started and controlled by the processing unit 209.

If the patient undergoes an ultrafiltration treatment, beyond the blood circuit the suction pump 3b connected to the outlet line of the fluid circuit 94 is started, so as to take by convection a fluid excess in the patient (beyond the dangerous substances/molecules).

Conversely, if the therapy that has been set comprises a haemofiltration treatment, beyond the blood circuit and the suction pump 3b for taking fluids by convection also the pump 3c on the inlet line of the fluid circuit 94 is started and the selecting means 97 placed so as to enable a post-infusion.

Also the infusion line 51 shall be used so as to enable a further addition of liquids to the post-infusion or to enable a suitable pre-infusion.

Conversely, if the treatment involves haemodialysis, the pumps 3c and 3b of the fluid circuit 94 shall be started and the selecting means 97 shall be positioned so as to ensure the passage of the dialyzing liquid only towards the filtration unit 5 so as to take substances and/or molecules and/or liquids by diffusion and possibly by convection if the transmembrane pressure through the filtration unit is other than zero.

Eventually, if a haemodiafiltration treatment has to be carried out, beyond the blood circuit the fluid circuit and therefore the pumps 3c and 3b shall be started, so as to ensure a circulation of the liquid within the filtration unit 5 and also the pump 3d of the infusion line 51 shall be started so as to ensure a pre- or post-infusion.

Obviously, it will be possible to set up different therapies comprising one or more of the treatments referred to above.

In all the treatments described above, possibly except the ultrafiltration treatment, it will be possible to use the auxiliary pre-infusion line for introducing an anticoagulant and/or a suitable infusion liquid into the blood.

Obviously, the anticoagulant can also be administered by means of the suitable device 90 designed for the introduction of heparin into blood.

Concerning this it should be pointed out that the apparatus according to the invention is designed to receive various kinds of syringes according to the amount of anticoagulant to be administered.

Obviously, it is the control unit 209 that, being connected to the various devices, sensors, pumps and being input with the weight data from the various scales, is able—once it is set—to control and automate the whole working of the apparatus.

In further detail, it is possible to set the flows of the various pumps present on the apparatus in accordance with the therapy or therapies to be started.

Obviously, the suitable setting of said flows results in an amount of fluid taken from the patient (weight loss), which will generally be given by the difference between the weight of the liquid that has been collected in the bag 99 and of the liquid circulated in the circuit through the primary fluid container 95, the auxiliary fluid container 200 and the secondary fluid container 87.

In particular, in accordance with the data received by the control unit coming from the various scales (and the theoretical flow rates fixed on each pump of therapy/treatment carried out) the control unit 209 shall control the means for circulating fluid in the various lines by suitably varying the thrust exerted by the various pumps 3a, 3b, 3c, 3d, 3e.

In particular, the signals coming from the scales referred to above 205, 206, 207, 208 are used by the control unit 209 for determining the weight of the particular fluid introduced into the line or collected.

In order to determine the amount of fluid released or collected in a particular bag or container the control unit 209 compares at regular intervals (the greater the flows the smaller the intervals) the actual weight of the container with the desired weight (which is a direct function of the desired flow for each pump and of the time interval between each control step $\Delta W = Q \Delta t$).

The desired weight can be calculated as a function of the required flow (stored in a suitable storage unit of the computer) and of the time elapsed from the beginning of the treatment.

If the actual weight and the desired weight differ from each other, the control unit acts on the corresponding pump so as to reduce, and possibly cancel, said difference. In other words, during each cycle not an absolute weight variation, but only the variation in the time interval is taken into consideration to correct the latter.

The control unit takes into consideration variations in the difference starting from the last comparison, so as to avoid oscillations of the actual flow around the desired flow.

After the above description of the hydraulic circuit and of the possible working of the apparatus according to the invention incorporating said circuit, here is shown a detailed structure of the support element 4 according to the invention.

The support element as shown in the FIGS. 2 to 8a generally consists of a main body 6 and of a support structure 64 associated to said main body 6 and placed laterally with respect to the latter.

The main body 6 has a front wall 25 which is generally, though not necessarily, plane; then there is at least a peripheral wall 32 projecting away from the front wall 25 so as to define with the latter a housing compartment 33 designed to receive at least a portion of a fluid distribution circuit 15 to be associated to said support element.

Figure 2:
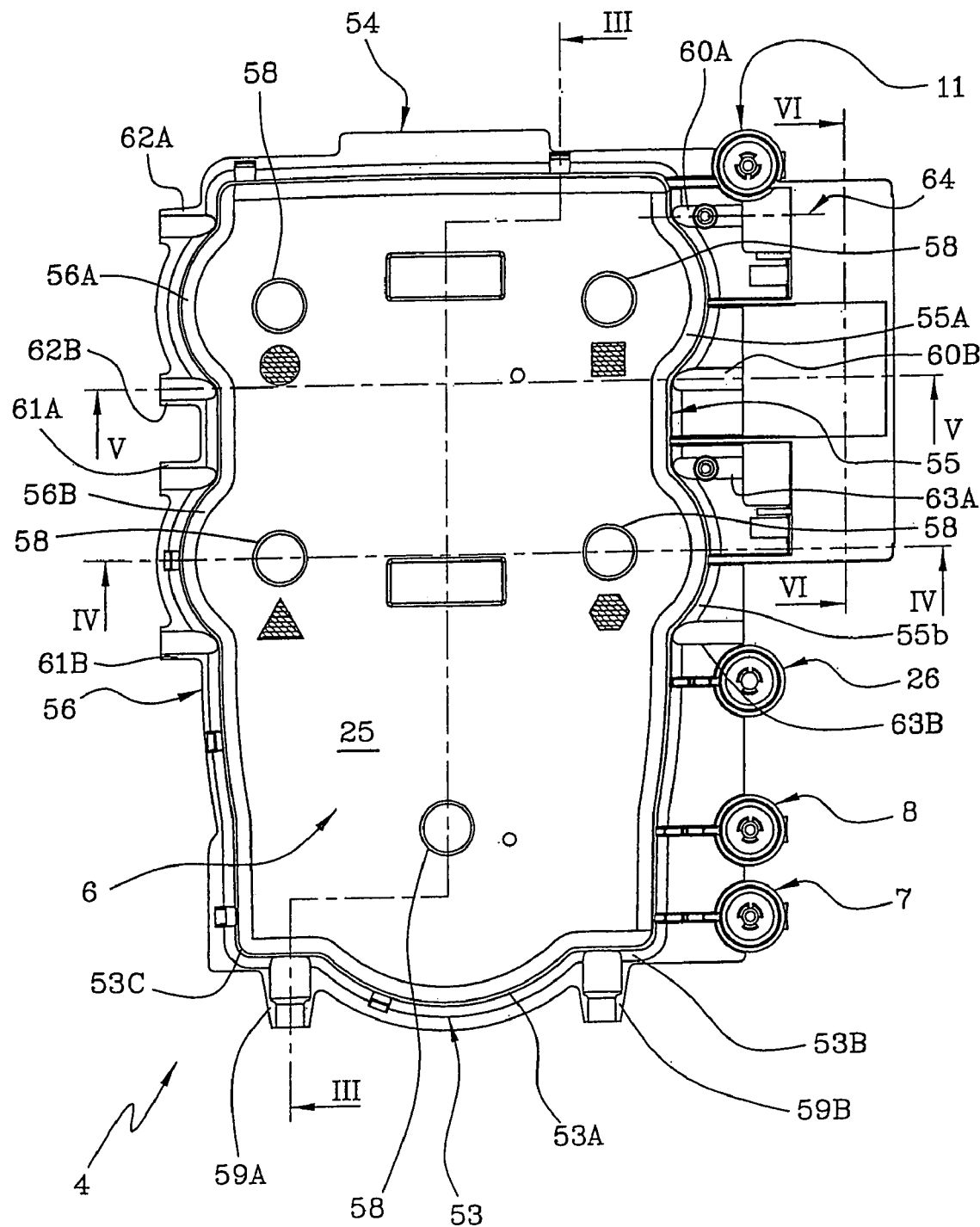
FIG. 2 shows a view from above of a support element according to the present invention.

As can be seen from FIG. 2, the front wall 25 is delimited by a given number of sides 53, 54, 55 and 56, and the peripheral wall 32 projects away from each of said sides.

It should be noted that the sides referred to above are basically rectilinear and, generally, at least first sides 55, 56 and at least second sides 53, 54 can be identified, which are basically parallel and facing each other.

In other words, in a view from above the support element 4 has an approximately quadrangular shape and its front wall 25 is delimited by first opposite longer sides 55, 56 with a basically rectilinear development and having each two curved portions 55a, 55b; 56a, 56b whose cavities face their respective opposite side.

In further detail each of said curved portions 55a, 55b; 56a, 56b can be defined by an arc of circle.

Then there are second opposite shorter sides 53, 54, whose development is again basically rectilinear; at least one of said second sides 53, 54 has a curved portion 53a placed between two rectilinear lengths 53b, 53c, which has in its turn a cavity facing the opposite side.

Here again the curved portion 53a can be defined by an arc of circle.

As can be further noted by simply observing FIG. 2, the arc of circle defining the curved portion 53a has a greater radius of curvature than the curved portions 55a, 55b, 56a, 56b defined on the first opposite longer sides 55, 56, as shall be better explained later.

Examining now the peripheral wall 32 (see FIGS. 7 and 8), it can be noted that it has at least a portion projecting away from each of the sides of the support element 4.

Generally, there will be at least one portion projecting from the first opposite sides 55, 56, and one projecting away from each of the second opposite sides 53, 54.

It is also evident that the peripheral wall 32 can also be discontinuous, i.e. it can have cavities or interruptions provided that it globally enables to define the aforesaid housing compartment 33.

Figure 7:
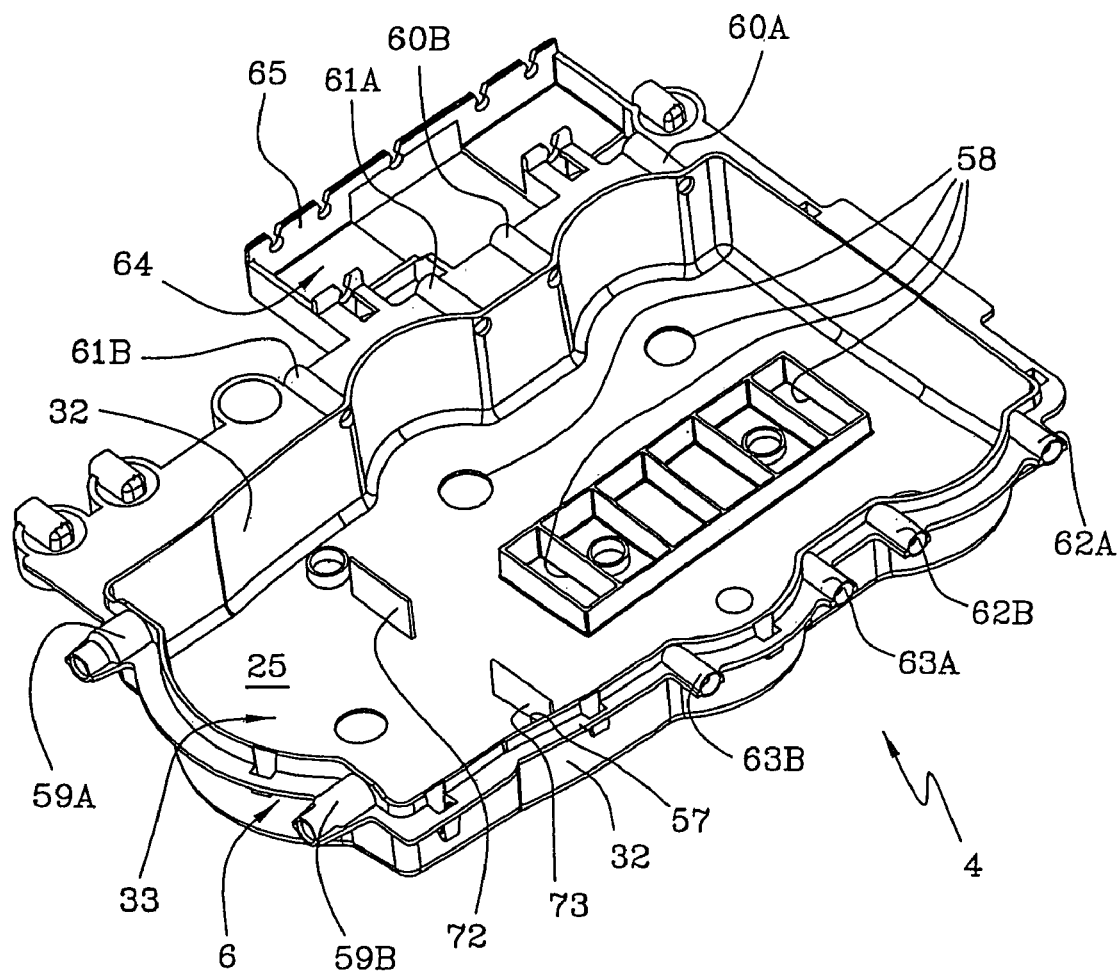
FIG. 7 shows a perspective view from a first side of the support element of FIG. 2.
Figure 8:
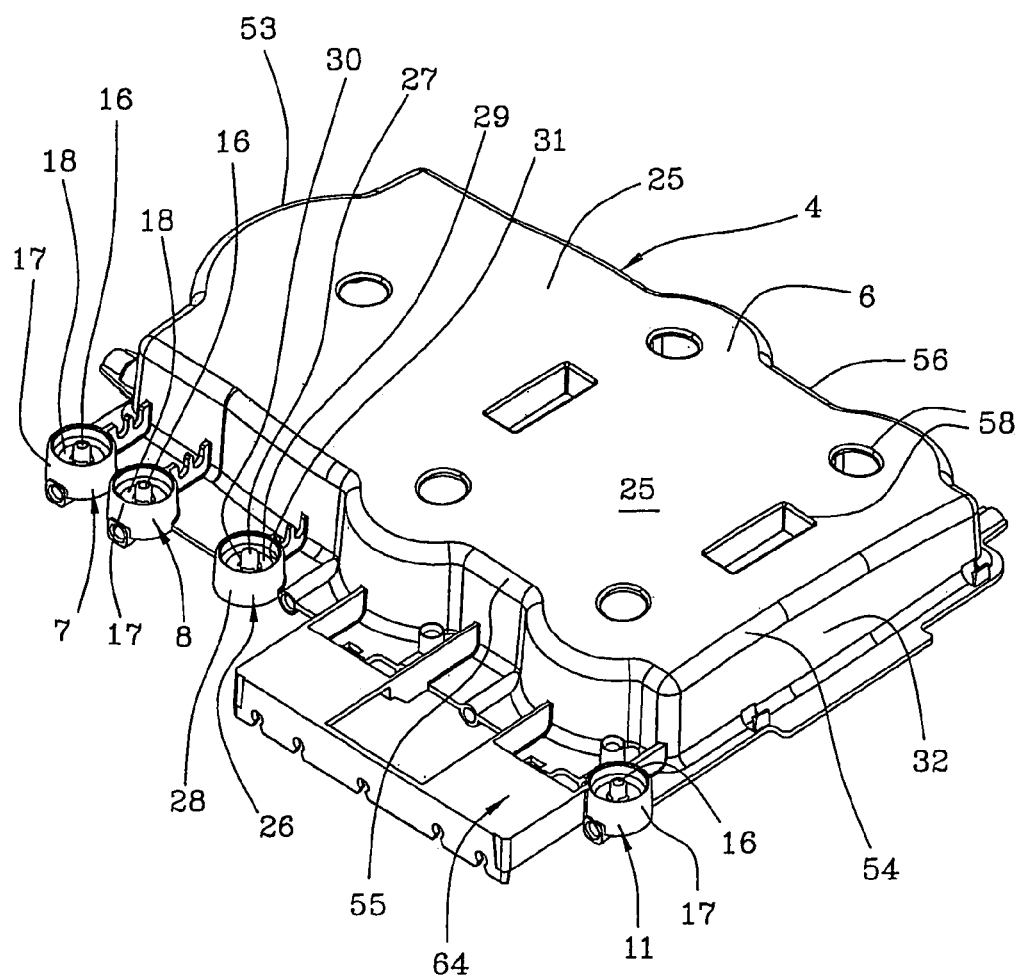
FIG. 8 shows a perspective view from the opposite side of the support element of FIG. 7.

The embodiment shown in FIGS. 7 and 8 is characterized in that the peripheral wall 32 projects away from all the sides of the front wall 25 and defines a basically continuous surface delimiting the housing compartment 33.

In other words, the housing compartment 33 has an access opening 57 without any kind of closing wall, which access opening is designed to face—when the support element 4 is being used—the extracorporeal blood treatment apparatus 2.

Figure 3:
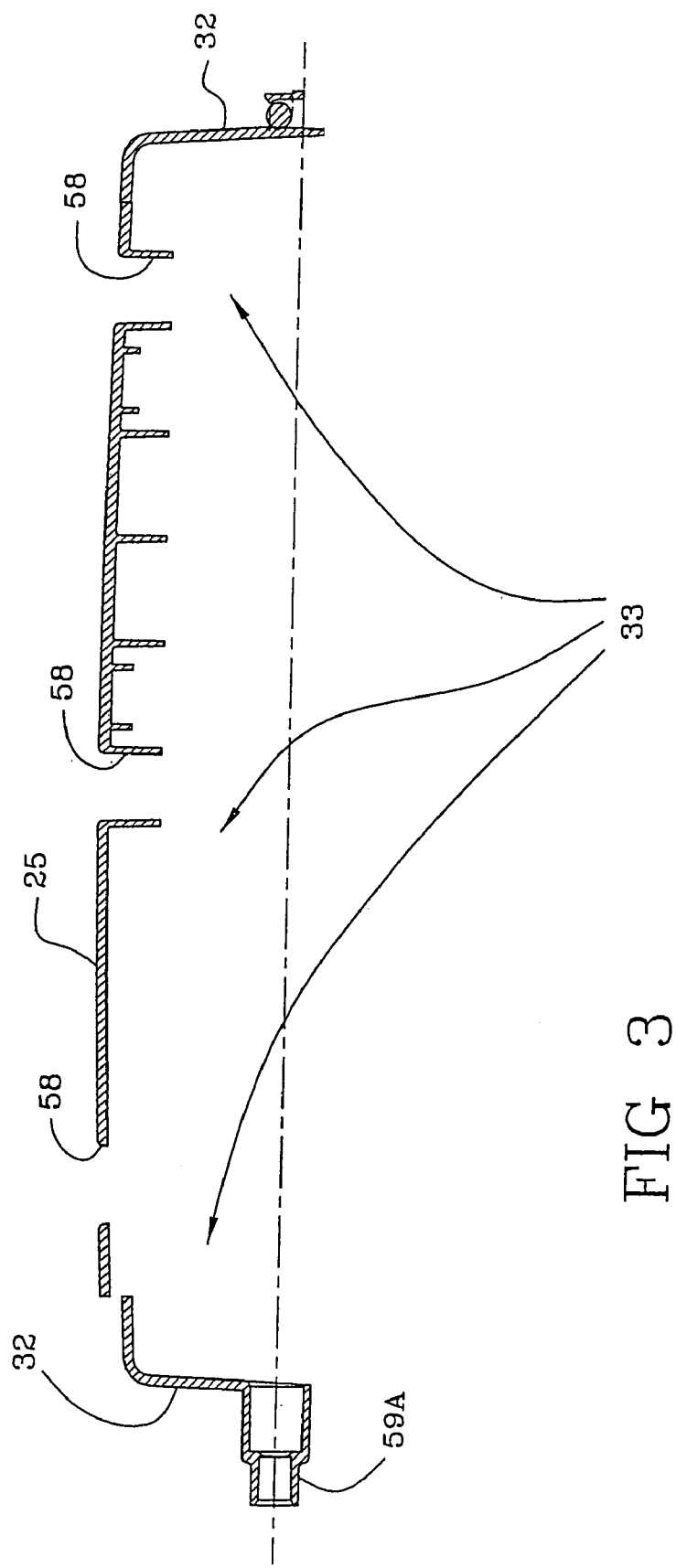
FIG. 3 shows a section of the module of FIG. 2 according to line III—III.
Figure 4:
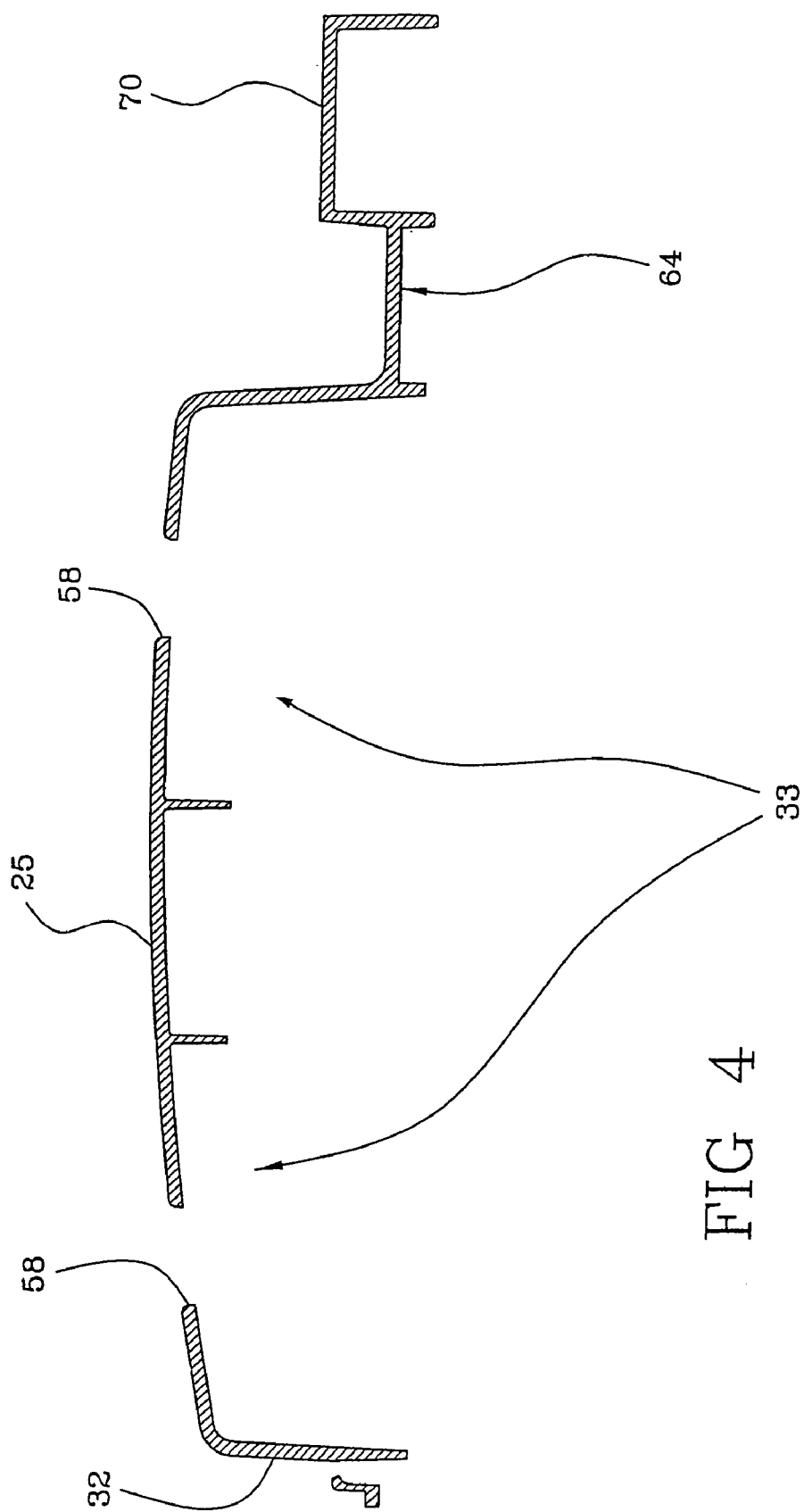
FIG. 4 shows a further section of the element of FIG. 2 according to line IV—IV.
Figure 5:
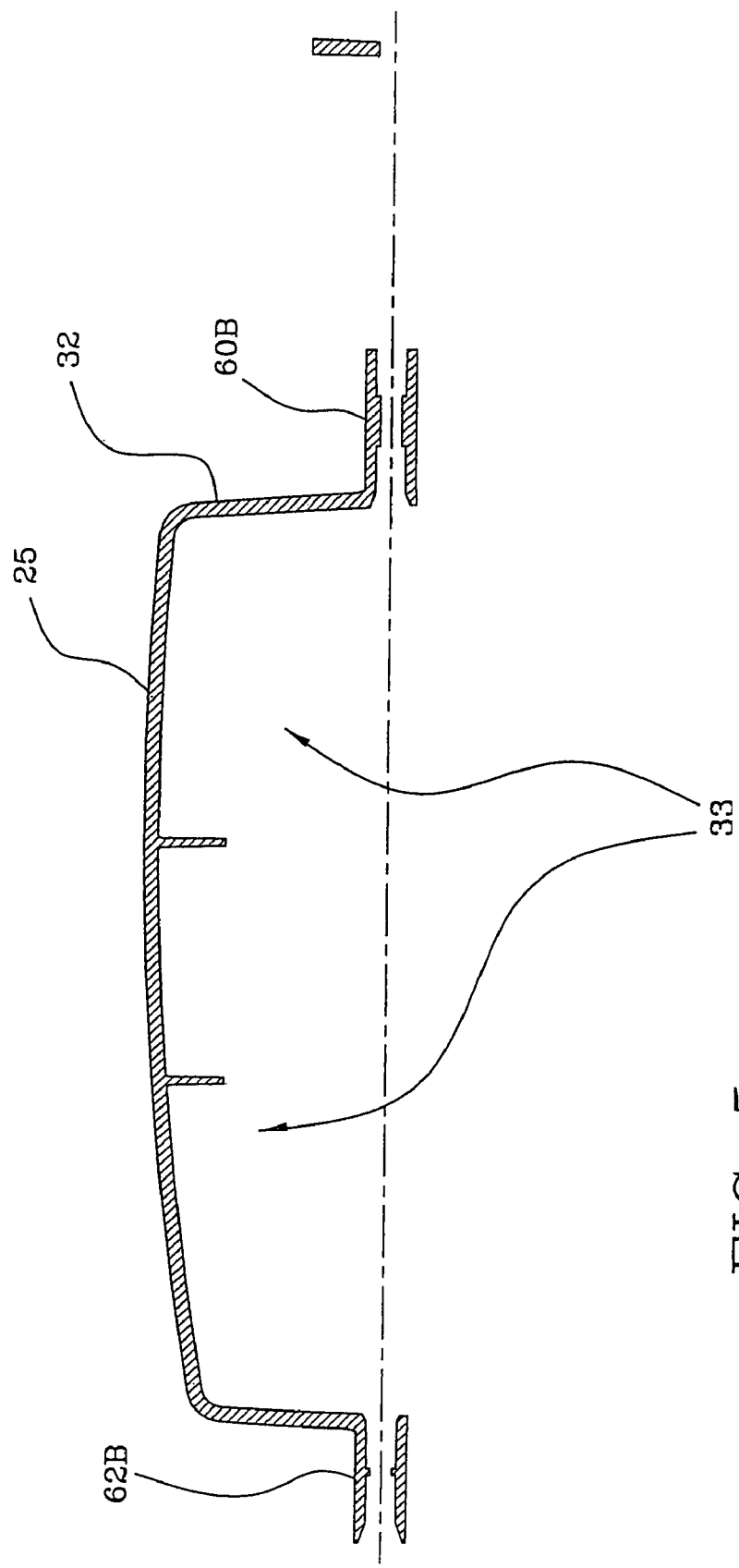
FIG. 5 shows again a section according to line V—V of FIG. 2.

Moreover, from FIGS. 3, 4, 5 it can be inferred how sections according to a plane transversal with respect to the front surface, and in particular sections according to planes orthogonal to said front surface 25, show that the main body has a substantially C-shaped profile.

The peripheral wall 32 defines the two end lengths of said C, whereas the front wall 25 defines the intervening elongated length.

It should be noted how the front wall 25 and the peripheral wall 32 define a main body 6 having a box-shaped structure basically closed on five out of its six faces.

Said arrangement results in that, however sectioning the support element 4 according to two planes orthogonal one to the other and transversal to the front surface 25, the main body 6 will have C-shaped sections that are also orthogonal one to the other.

See in particular for instance the sections of FIGS. 3 and 4.

In still other words, the support element 4 comprises a front wall 25 which is able to connect opposite peripheral walls projecting in a basically perpendicular direction from said front wall 25.

As shown in FIGS. 2, 7 and 8, the front wall 25 has a given number of through openings 58 putting into communication the housing compartment 33 with the outside environment while the support element is being used.

Referring in particular to the figures described above, it can be noted that there is at least an opening 58 on each of the curved portions 53a, 55a, 55b, 56a and 56b and that said openings are defined by concentric round holes placed on the same axis as the respective arcs of circle defining the curved portions.

As far as the materials used are concerned, it should only be pointed out that the main body will be made of a stiff material, plastic for instance, which can protect the various tube lengths and/or elements therein contained.

It is also possible to carry out the whole support element or only a part of it with a material that is also transparent so as to obtain a visual access to the housing compartment 33.

Going into deeper structural details and referring in particular to FIG. 7, it can be noted that there are several engagement connectors fastened to the respective sides of the box-shaped body.

In particular, there are at least a first and a second engagement connector 59a, 59a placed laterally with respect to the curvilinear length 53 of one of said second sides 53.

Said connectors shall be secured and generally carried out as one piece with said rectilinear lengths 53b and 53c.

There are also pairs of engagement connectors 60a, 60b, 61a, 61b, 62a, 62b, 63a, 63b respectively engaged near each of the curved portions 55a, 55b, 56a, 56b of the first longer sides 55, 56.

In other words, there will be two of said connectors placed exactly on opposite ends of each of the curved portions.

As in the case of the previous connectors, also the engagement connectors 60a, 60b, 61a, 61b, 62a, 62b, 63a, 63b are carried out as one piece with the main body 6.

Furthermore, all the aforesaid connectors are fastened to the peripheral wall 32, for instance on a free edge of said peripheral wall.

As can be seen in the section of FIG. 5, each engagement connector defines a gap leading towards the housing compartment 33.

Figure 7A:
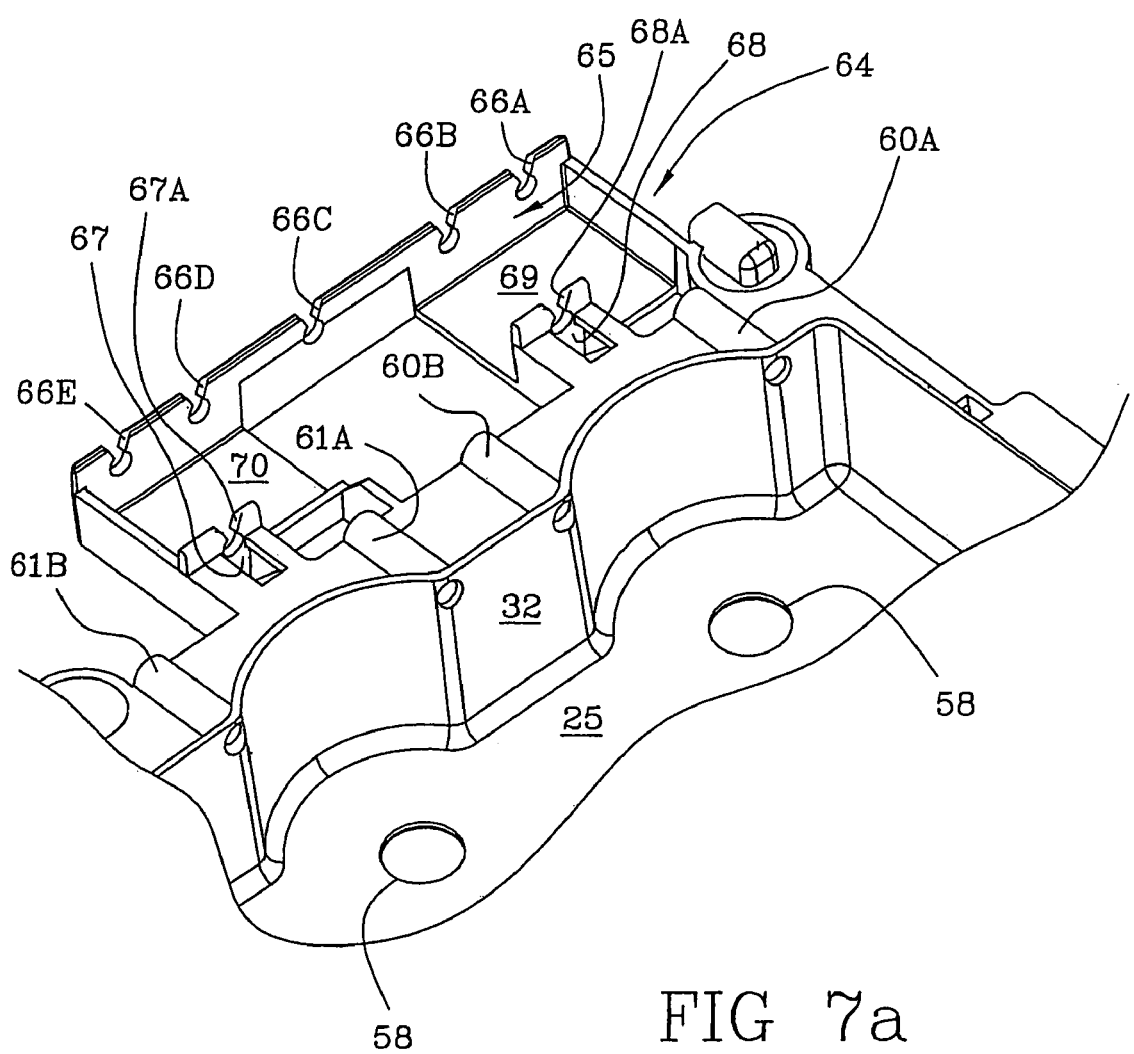
FIG. 7*a* shows an enlarged detail of the element of FIG. 7.
Figure 8A:
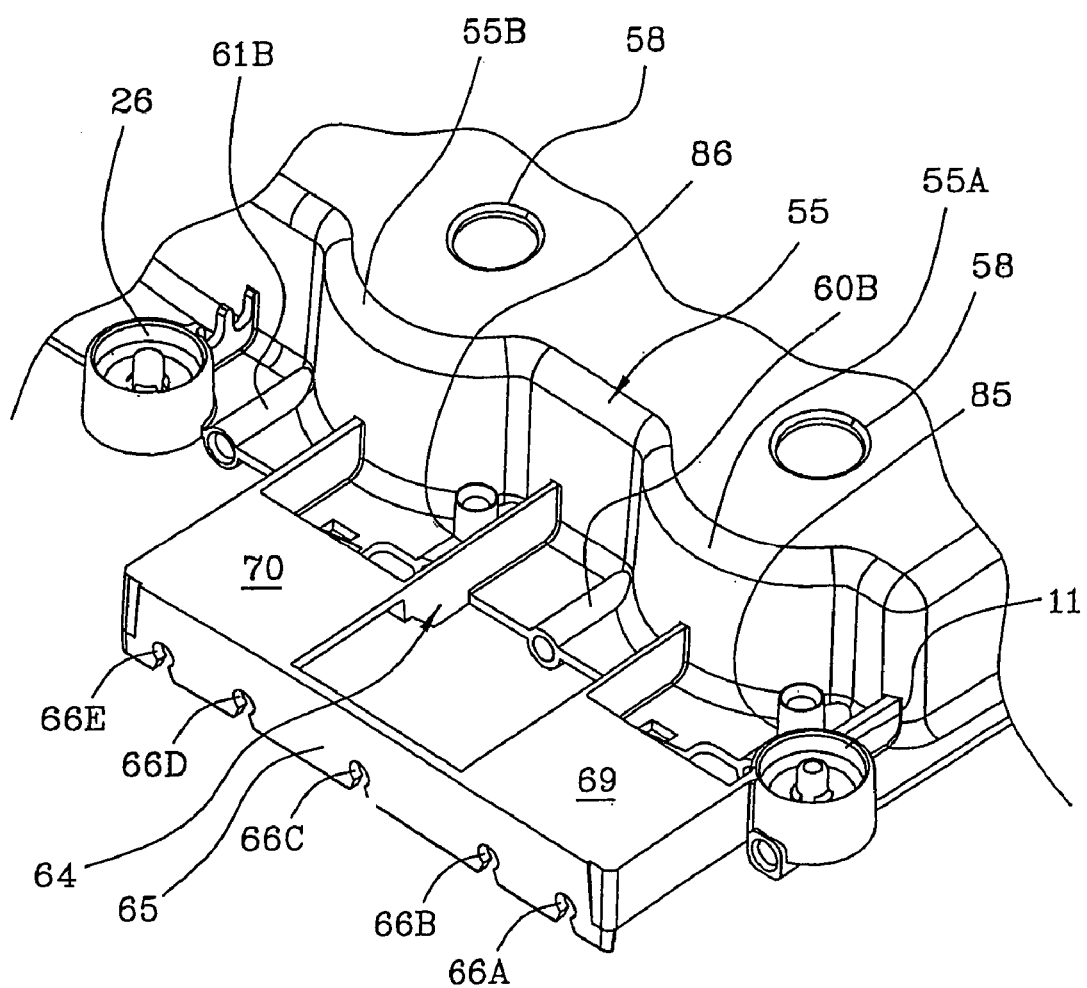
FIG. 8*a* shows an enlarged detail of the element of FIG. 8.

Referring now to FIGS. 7a and 8a, it can be noted how the support structure 64 associated to the main body 6 is positioned laterally with respect to the latter.

Also the support structure 64 is stiffly secured to the main body and will generally be carried out as one piece with the latter.

It should be pointed out that the support structure 64 is engaged to the main body 6 on one of the first longer sides 55, 56 and, in further detail, on the curved portions 55a, 55b of said fist longer side 55.

The support structure 64 is equipped with a positioning fin 65 (see again FIGS. 7a, 8a and the section of FIG. 6), which has a given number of main seats 66a, 66b, 66c, 66d, 66e suitably placed so that respective tubes of the fluid distribution circuit 15 associated to the support element 4 can be engaged therein.

Referring to the relative position of the various components of the support structure 64, it can be noted how at least two, and generally three of said main seats 66a, 66c, 66d are placed on their respective engagement connector 60a, 60b, 61a located near the curved portions 55a, 55b of one of the first longer sides 55.

Figure 9:
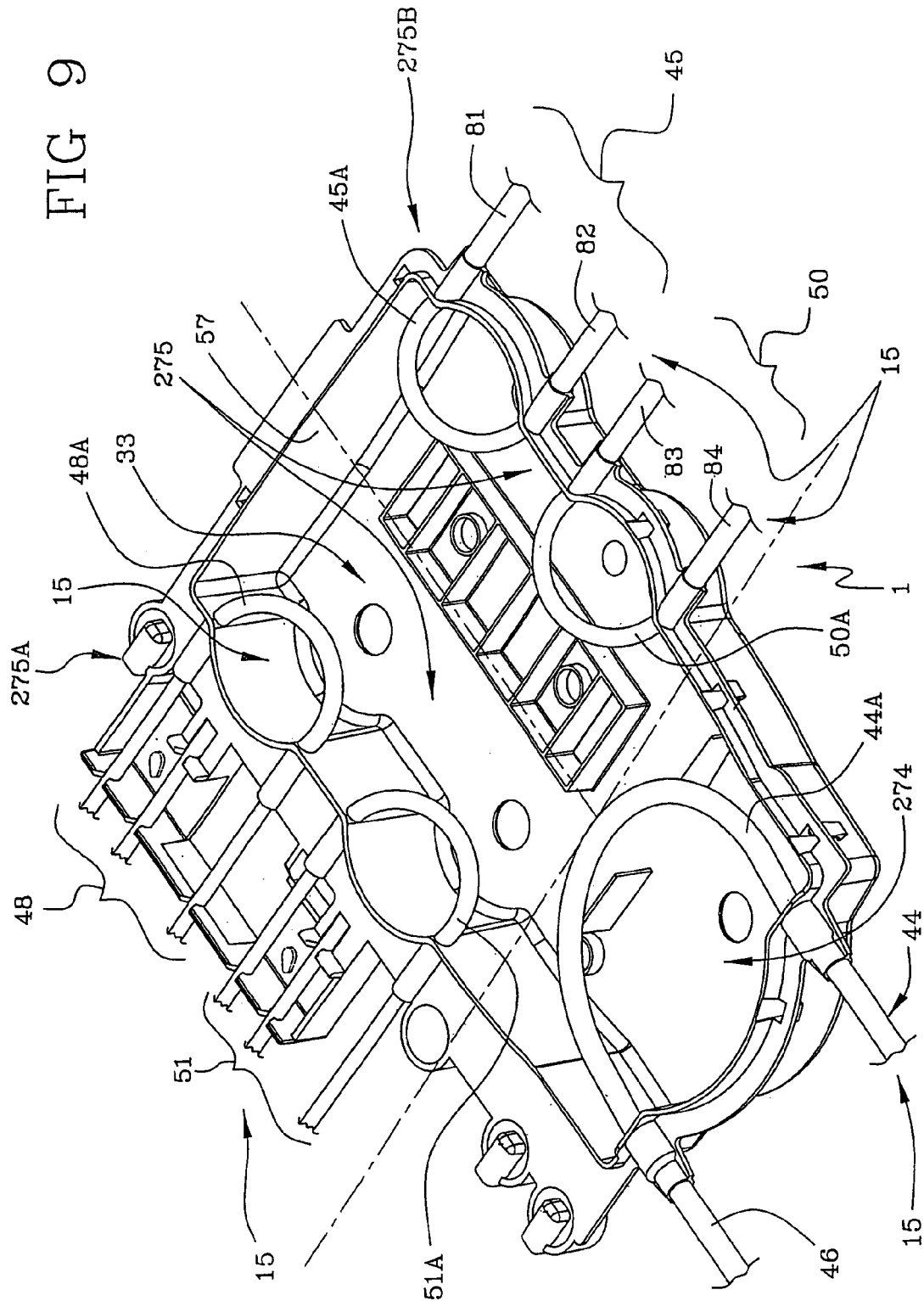
FIG. 9 shows a perspective view of an integrated module according to the present invention.

In other words, the three main seats 66a, 66c, 66d and their respective connectors 60a, 60b, 61a are positioned so as to receive parallel tube lengths (see to this end FIGS. 9 and 9a).

Figure 6:
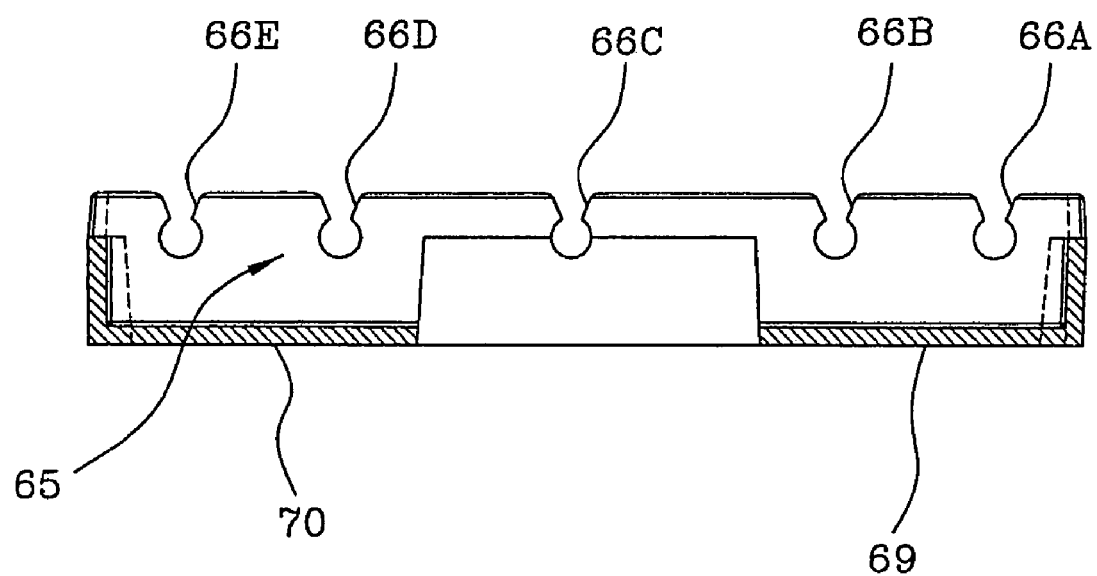
FIG. 6 shows a section according to line VI—VI of the support element of FIG. 2.

Going back to FIG. 6 and to FIGS. 7a and 8a, it can be noted how the positioning fin 65 comprises two further main seats 66b and 66e and how also the support structure 64 is equipped with two auxiliary portions 67 and 68, each of them being provided with a respective auxiliary seat 67a, 68a so that the latter can cooperate with one another thus enabling the positioning of tube lengths parallel one to the other and generally parallel to those present on the three main seats and on the three engagement connectors referred to above (see again FIGS. 9 and 9a).

The support structure 64 then comprises at least a first covering wall 69 lying on a plane parallel to the plane of the front wall 25 so as to cover at least two parallel tube lengths in operating conditions in which the support element is engaged to the apparatus.

Figure 16:
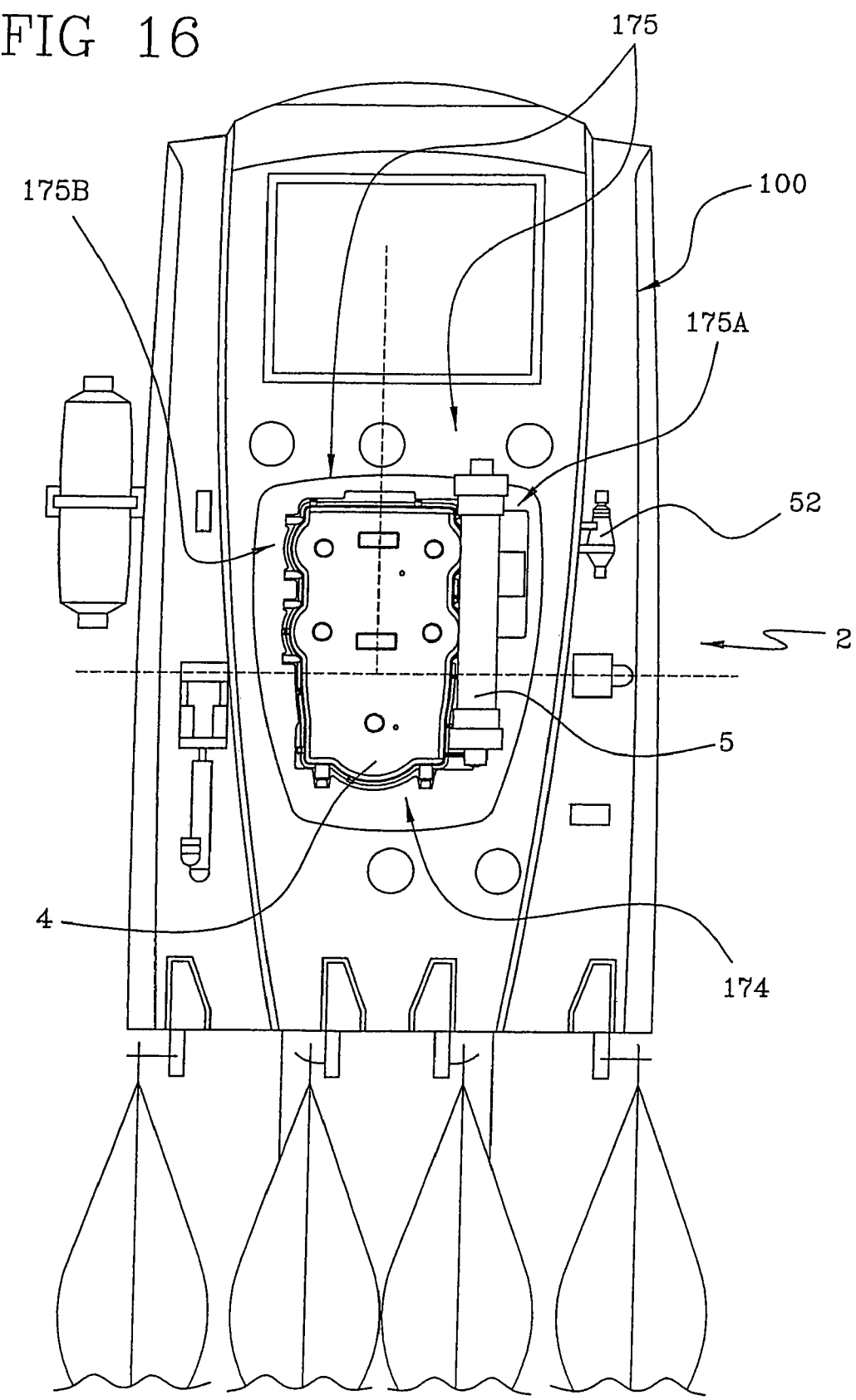
FIG. 16 shows a front view of the apparatus of FIG. 15 with an integrated module without the hydraulic circuitry thereto associated.

Compare to this end FIGS. 9 and 16.

In a wholly specular way the support structure 64 comprises at least a second covering wall 70 lying again on a plane parallel to the plane of the front wall 25 so as to cover at least two further parallel tube lengths when the support element is again in operating conditions.

Referring to FIG. 8 it should then be pointed out that the support element 64 has a smaller height than—or at the most the same height as—the peripheral wall 32 of the main body.

This means that the support structure 64 has been designed so as not to increase the height of the whole support element.

Figure 14:
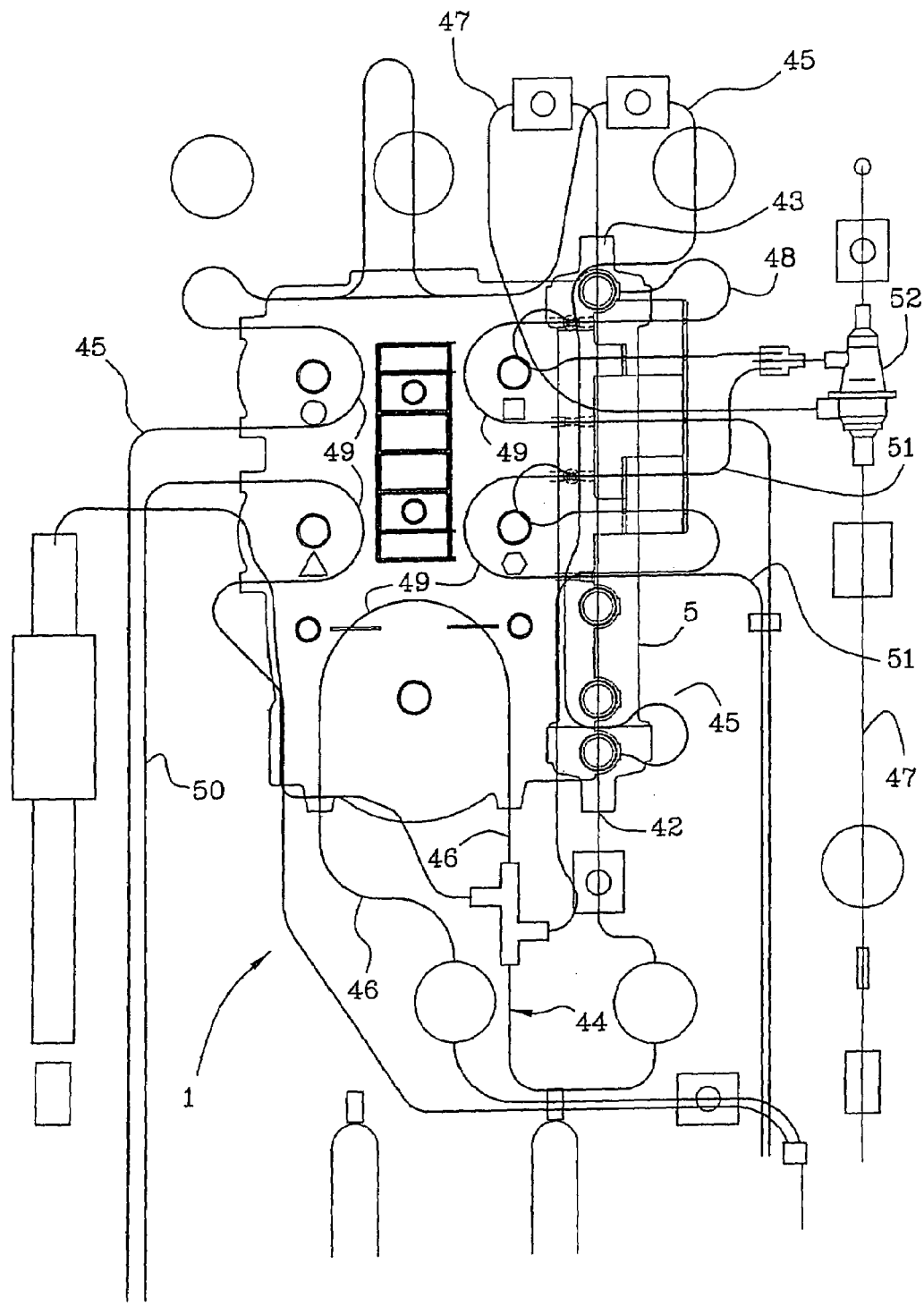
FIG. 14 shows a schematic view of the integrated module that can be associated to the apparatus, equipped with the hydraulic circuitry.

Referring now to FIG. 7, further note at least one and in generally two positioning projections 72 and 73 associated to the main body 6 and designed to enable the correct positioning of a tube length to be associated to the support element as shall be better explained later (see anyway FIGS. 9 and 14).

Said first and second positioning projections 72, 73 are placed inside the housing compartment 33 and are generally associated (or also carried out as one piece) to the front wall 25.

It should then be noted that the support element 4 comprises a main body 6 having at least a first and a second connector 7 and 8, spaced away from each other, in which corresponding counter-connectors 9 and 10 of the treatment unit 5 (see FIG. 11) are engaged.

The blood treatment unit 5 can for instance be a plasma filter, a haemodialysis filter, a haemofiltration filter, a haemodiafiltration filter or another type of unit.

The first and second connector 7 and 8 are directly engaged to the main body 6; in the examples shown said connectors are made of stiff plastic material and as one piece with the main body.

The support element 4 has a third connector 11 spaced away from the connectors 7 and 8 and engaged directly to the main body 6; in the examples shown also the third connector is made of stiff plastic material and as one piece with the main body; said three connectors define pairs of connectors having a differentiated central axis one with respect to the other for the engagement of corresponding pairs of counter-connectors associated to different blood treatment units that can be mounted onto the support element. Thus, one main body 6 can be used to carry out integrated modules with different features, thanks to the possibility of engaging treatment units 5 not only with different membranes but also with different global size and therefore with different central axis of the corresponding counter-connectors. Each of the connectors 7, 8, 11 referred to is a stiff support and defines a fluid passage having a first end portion 12, designed to be put into fluid communication with a corresponding channel 13 present in the respective counter-connector 9, 10 housed in the treatment unit 5 (see also the sections of FIGS. 12 and 13); each connector 7, 8, 11 also has a second end portion 14, designed to be put into fluid communication with a fluid distribution circuit 15 to be associated to the main body 6. Going into further structural detail, each of said connectors 7, 8, 11 comprises a tubular channel 16 defining said first portion, a sealing collar 17 placed radially outside the tubular channel, and a connection wall 18 developing without interruptions between an outer side surface 19 of the tubular channel and an inner side surface 20 of said collar. In practice, the outer side surface of the tubular channel, the inner side surface of the sealing collar and the connection wall define a ring-shaped engagement seat 21, whose bottom is delimited by the connection wall, shaped so that a corresponding counter-connector of the treatment unit can be engaged therein. The tubular channel 16 is arranged coaxially with respect to the sealing collar 17, and both turn around a common symmetry axis. The ring-shaped seat 21 has an increasing radial size getting away from the bottom wall and comprises a first zone 22 near the bottom, having a constant radial size, a second zone 23, distal with respect to the bottom and with a constant radial size greater than the radial size of the first zone, and a third zone 24 between the first and the second zone, having a progressively increasing size getting away from the bottom wall 18. The tubular channel and the sealing collar of each connector 7, 8, 11 project parallel one to the other from the main body 6, so as to define one direction of coupling with the corresponding counter-connectors of a treatment unit 5. In the examples of embodiment shown the various connectors have a symmetry axis that is basically orthogonal with respect to a front surface 25 of the support element 4.

Figure 11:
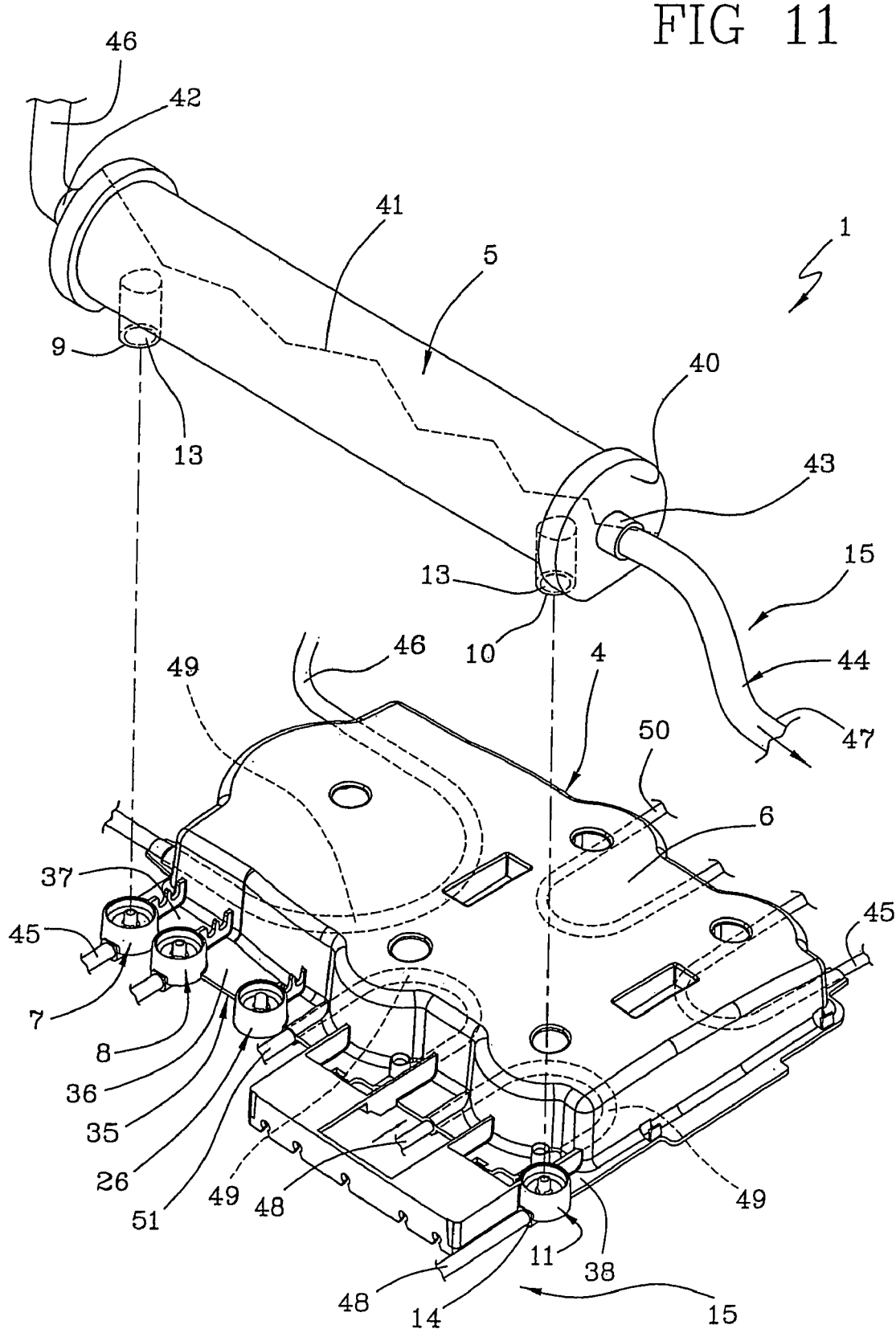
FIG. 11 shows the integrated module of FIG. 10 to which a blood treatment unit can be associated.
Figure 12:
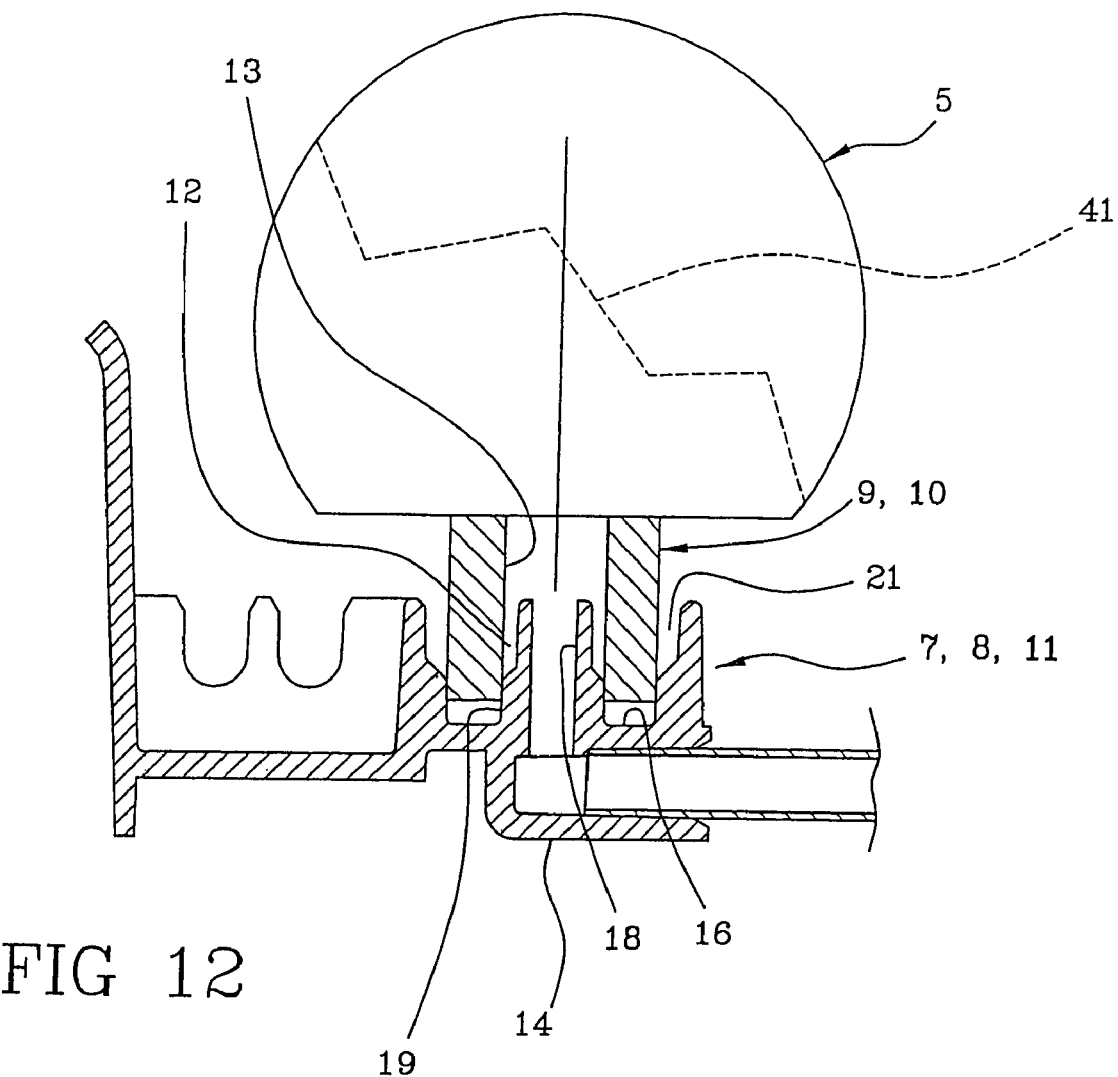
FIG. 12 shows a section of a connector of the support element and of a counter-connector of the blood treatment unit.
Figure 13:
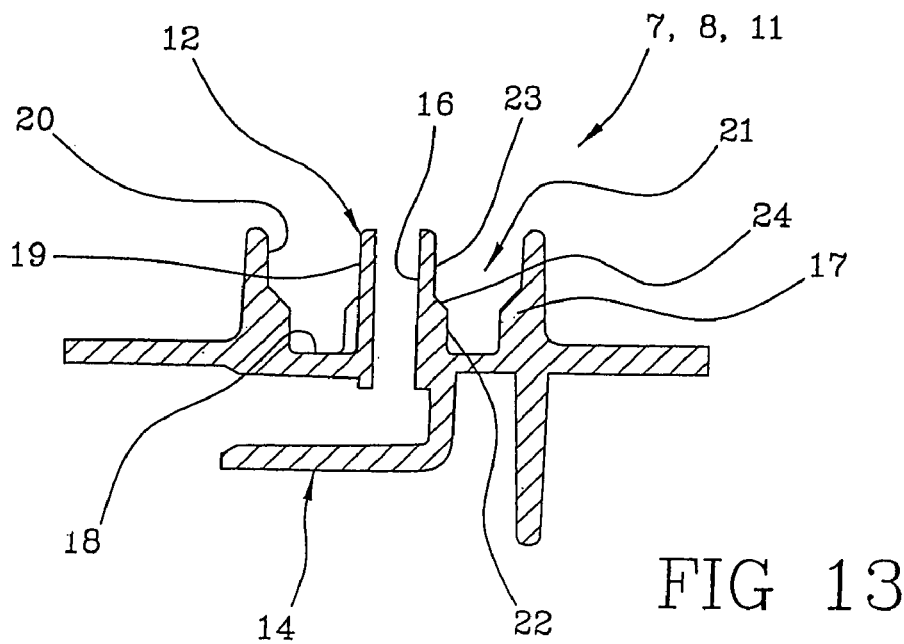
FIG. 13 shows a further section of a connector according to the present invention.

The support element shown also comprises a fourth connector 26 spaced away from said first, second and third connector; the fourth connector is also connected directly to the support element. In the example shown the fourth connectors is made of stiff plastic material and as one piece with the main body 6 and defines with at least one of the other connectors a further pair of counter-connectors associated to a blood treatment unit to be mounted onto the support element. The fourth connector comprises a central cylindrical positioning body 27, a sealing collar 28 placed radially outside the cylindrical body, and a connection or bottom wall 29 developing without interruptions between an outer side surface 30 of the cylindrical body and an inner side surface 31 of said collar. In practice, said fourth connector defines an engagement and flow-closing body for a counter-connector of the treatment unit 5. As shown in FIGS. 11, 12 and 13, the various connectors are made of stiff material so as to define a mechanical support of the treatment unit and, if needed, so as to define a passage or a blocking member for the fluid getting through the counter-connectors 9, 10. The four connectors that are present in the support element are aligned one with respect to the other and arranged on one side of said main body. More to the point, the main body of the element shown defines the aforesaid housing compartment 33, which can house at least a portion of the fluid distribution circuit 15 designed to be associated to the support element 4. The housing seat has an open side 57 ensuring a suitable fitting and positioning of the integrated module 1 onto the apparatus 2, as shall be disclosed later in further detail. The support element then has an auxiliary structure 35 extending laterally and outside with respect to the operating seat from a base zone 36 of the peripheral wall 32. The four connectors come out from the auxiliary structure the first, second and fourth 7, 8, 26 are placed one beside the other and are arranged on a first end zone 37 of the auxiliary structure, whereas the third connector 11 is placed on a second end zone 38 placed opposite the first one.

Figure 10:
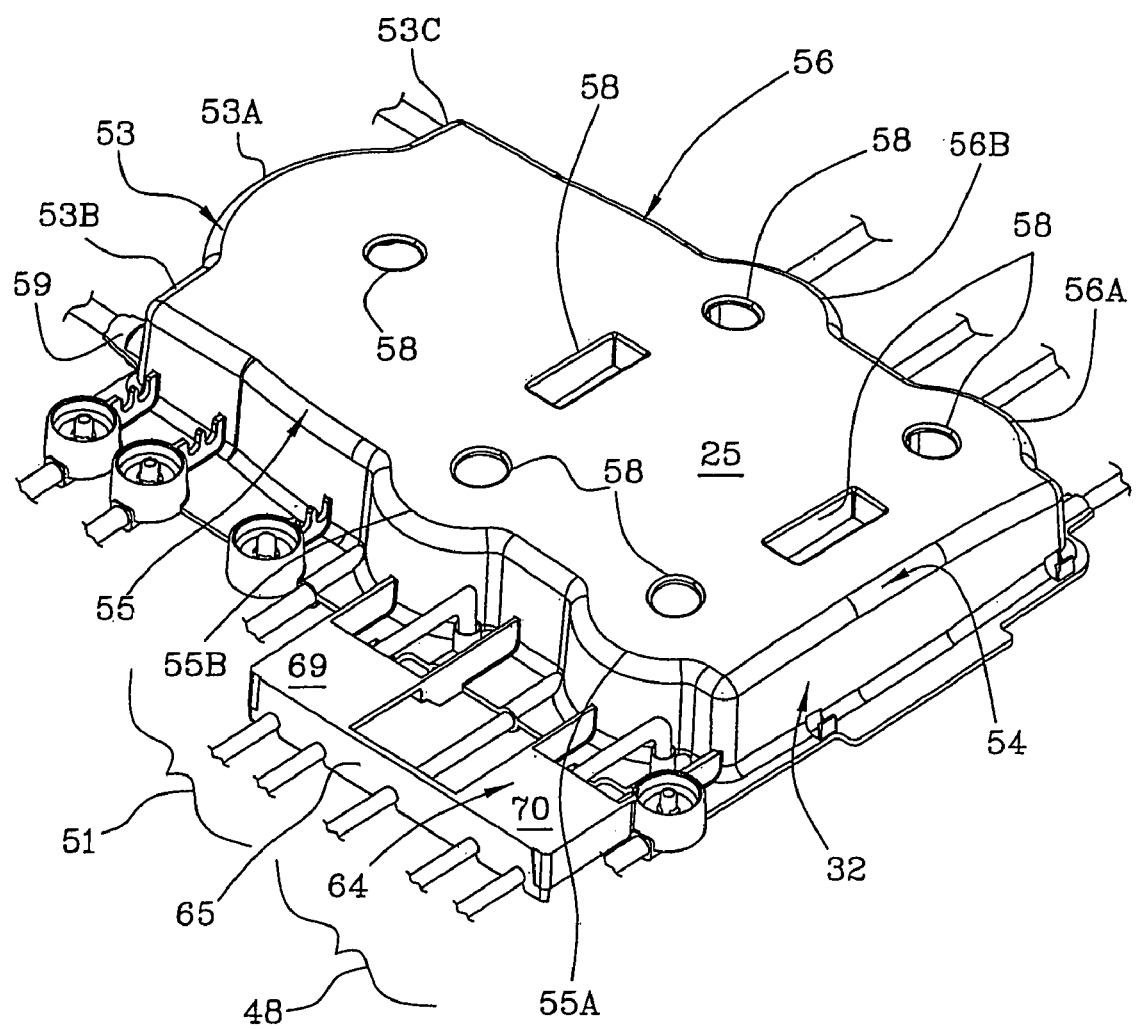
FIG. 10 shows a perspective view from the opposite side of the module of FIG. 9.
Figure 10A:
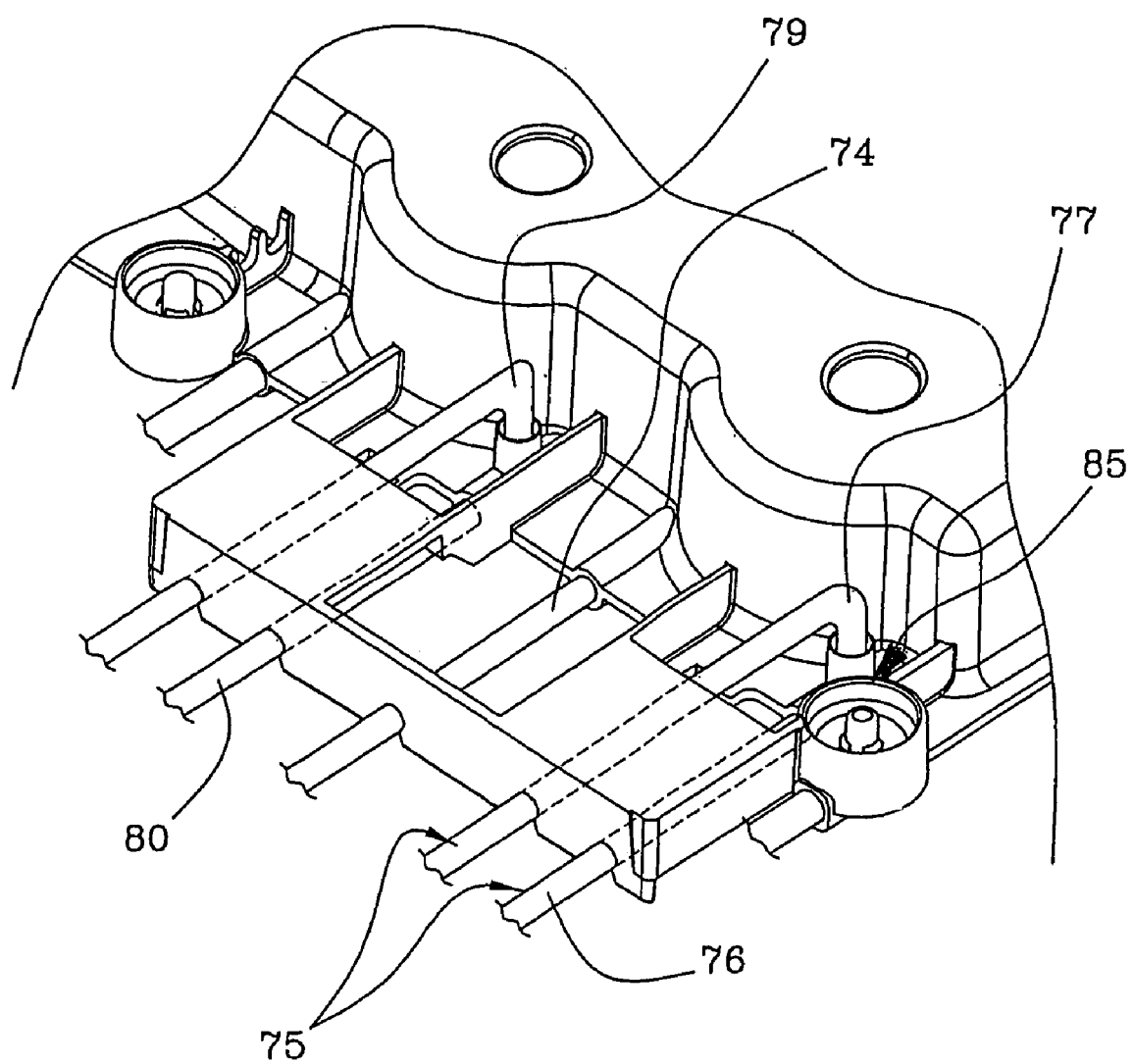
FIG. 10*a* shows an enlarged detail of the module of FIG. 10.

A support element according to the invention can be suitably used for carrying out an integrated module, such as for instance the one shown in FIGS. 9–11, in which the support element of FIGS. 2–8 is used by way of example. As can be seen, the treatment unit 5 is fastened to the support element 4 on at least the pair of connectors; the treatment unit comprises a housing body 40, at least a semipermeable membrane 41 (for instance with parallel hollow fibers or with plates) operating inside the housing body and defining a first chamber and a second chamber; a first and a second counter-connector are associated to the housing body and secured to their respective connectors housed by the main body 6 (see for instance FIG. 11).

The first and second counter-connector 9, 10 have a tubular shape and are put into fluid communication with the second chamber of the treatment unit and with respective end portions 12 of said connectors. The treatment unit then has an access port 42 leading to the first chamber, and at least an exit port 43 from said first chamber, for the connection with an extracorporeal circulation line 44 for blood or another physiological fluid.

A fluid distribution circuit 15 is engaged to the support element 4 and cooperates with the treatment unit 5.

In further detail said circuit comprises the aforesaid blood line 44, which is fastened to the support element 4 on one of the second sides 53, 54 and has the curved portion 53*a*.

The blood line 44 is secured to the support element so as to define at least a tube length basically arranged as a U 44*a* with respect to said support element.

Said arrangement is related to the fact of enabling the cooperation between said tube length 44*a* and a respective pump 3*a* while assembling the integrated module onto the apparatus 2.

As can then be inferred from the appended figures, the U-shaped tube length 44 extends inside with respect to the peripheral wall 32 of the support element 4.

The positioning projections 72, 73 previously described act on the U-shaped tube length 44*a* so as to keep its correct position.

As can be inferred from FIGS. 1 and 9, the length 44*a* of the blood line 44 secured to the support element is defined by the intake branch 46.

The distribution circuit 15 then has the aforesaid inlet line 48 supplying fresh dialysis liquid.

Said line is fastened to the support element on one of the first longer opposite sides 55, 56, as can be seen in FIGS. 9, 9*a*, 10 and 10*a*.

Also the inlet line 48 is secured to the support element so as to define at least a tube length basically arranged as a U 48*a* with respect to said support element.

Also the tube length 48 is designed to cooperate with a respective pump 3*c* and is placed inside with respect to the peripheral wall 32 of the support element.

Referring to FIG. 9*a* it can be noted how the inlet line 48 is fastened to the main body 6 on the support structure 64, and how at least an inlet length 74 of the inlet line 48 is engaged into a main seat 66*c* of the positioning fin 65, as well as to the respective engagement connector 60*b*.

Analogously, at least an outlet length 75 of the inlet line is engaged into a main seat 66*a* of the positioning fin 65 and to the respective engagement connector 60*a*.

When engaged, the respective connectors and inlet and outlet lengths 74 and 75 are placed in a rectilinear arrangement and are parallel one to the other (see FIG. 9*a*).

As can further be seen (see in particular FIG. 10*a*), the outlet length 5 has a branching 85 splitting up into intake branch 76 conveying the fluid to the blood treatment unit 5, and into infusion branch 77 conveying the fluid into the blood line 44.

Said branching 85 is defined on the engagement connector 60*a* having a T shape with an inlet and two outlets.

Also the infusion branch 77 is secured to a main seat 66*b* and to an auxiliary seat 77*a*.

The infusion branch 77 and the intake branch 76, when engaged to the support structure 64, are placed in a rectilinear arrangement and are parallel one to the other.

The fluid distribution circuitry 15 then comprises at least the infusion line 51, which is also fastened on one of the first longer opposite sides 55, 56.

Said infusion line defines a tube length arranged as a U 51*a* with respect to said support element 4, so as to be able to cooperate, when in use, with a respective pump 3*d*.

Also the U-shaped tube length 51*a* extends inside with respect to the peripheral wall 32 of the support element.

Also the infusion line is secured on the support structure 64 and at least an outlet length 78 of the infusion line 71 is engaged into a main seat 66*d* of the positioning fin 65 and to its respective engagement connector 61*a* as shown in the appended figures.

In a wholly specular way to the intake line, the outlet length 78 has a branching 86 splitting up into pre-infusion branch 79 conveying the fluid to an intake branch 46 of the blood line 44, and into post-infusion branch 80 conveying the fluid to a blood return branch 47 of the blood line.

Here again there is an engagement connector 61*a* having a T shape so that the branching 86 into pre-infusion branch 79 and into post-infusion branch 80 is defined exactly by said connector 80.

The pre-infusion branch 79 is then fastened to an auxiliary seat 68*a* and to a further main seat 66*e* of the positioning fin 65.

When engaged to the support structure, said two branches 79 and 80 are placed in a rectilinear arrangement and are parallel to one another.

The fluid distribution circuit 15 then has the discharge line 45 secured to the support element also on one of said first longer sides 55, 56.

Said discharge line 55 defines at least a tube length arranged as a U 45*a* with respect to the support element, which tube length is also designed to cooperate with a respective pump 3*b* and extending inside with respect to the peripheral wall 32 of the support element.

The discharge line 45 is secured to the main body 6 on an opposite side with respect to the support structure 64 and the respective inlet length 81 and outlet length 82 are engaged into corresponding engagement connectors 62*b*, 62*a*.

Eventually, the distribution circuit 15 has the auxiliary pre-infusion line 50.

The latter is fastened to the support element 4 on one of said first longer sides 55, 56 so as to define at least a further tube length arranged as a U 50a with respect to said support element.

Also the tube length 50a is designed to cooperate, when in use, with a respective pump 3e and extends inside with respect to the peripheral wall 32 of the support element.

In other words, the housing compartment 33 is designed to house all U-shaped tube lengths of the various lines of the distribution circuitry 15.

The auxiliary pre-infusion line 50 is secured to the main body on an opposite side with respect to the support structure 64 and the respective inlet length 83 and outlet length 84 are engaged to engagement connectors 63b, 63a.

It should then be pointed out that the particular shape of the peripheral wall 32 of the support element 4 defining the arched portions and the peculiar position of the engagement connectors of the various tubes result in that the length of every free U-shaped tube portion 44a, 45a, 48a, 50a, 51a is smaller than or the same as $\pi R+2R$, where R is the radius of curvature of the tube length.

The peculiar shape of the integrated module is such that the free lengths within the housing compartment 33 are as short as possible in accordance with the radial sizes of the respective pumps which have to generate the flow within said tubes.

It should then be noted how the U-shaped tube length 44a of the blood line is longer than the tube lengths 45a, 48a, 50a, 51a defined by the further fluid lines having indeed a longer radius of curvature.

Moreover, the tube length of the blood line can be carried out, if needed, with materials differing from those of other tubes and/or it can have sections for the passage of fluid differing from the other tubes.

From the point of view of the geometrical position of the various tube lengths on the support element note the following.

First of all, the support element can be ideally divided into several zones comprising a first zone 274 secured to the portion of the blood line 44 which, in operating conditions of the module 1 engaged to the apparatus 2, shall be defined by the lower zone of said module.

Therefore, there will be a second zone 275 opposite the first zone, to which all the further fluid lines 45, 48, 50 and 51 are secured.

Said second zone consists in its turn of at least two ideal half-parts placed side by side 275a, 275b.

The tube length 45a of the discharge line 45 and the tube length 50a of the auxiliary pre-infusion line 50 will be fastened to the second half-part 275b.

Conversely, the tube length 48 of the intake line and the tube length 51a of the infusion line are fastened to the first half-part 275a. Said splitting into first and second zone 274, 275 and the two half-parts 275a, 275b of the second zone have been ideally shown in FIG. 9 by means of hatched lines.

As can be noted, the first and second half-part 275a, 275b of the second zone 275 are reciprocally placed side by side and generally perfectly symmetrical to a longitudinal axis of the main body 6. Should the first zone 274 be geometrically delimited, it could be defined as the area limited by at least one of the second sides 53 (having the curved portion and to which the blood line is secured) and by about half the length of the first opposite longer sides 55 and 56 near the second side 53.

Analogously, the second zone 275 is partly delimited by one of said second sides 54 which has no curve and by a portion of the first opposite longer sides 55 and 56 near said second side 54.

The assembly process of an integrated fluid treatment module comprises the stage of installation of a support element 4, for instance as shown in FIGS. 2–8, and a treatment unit 5 to be coupled to the support element. Then the blood treatment unit is fastened to the support element. Eventually, a fluid distribution circuit 15 is associated to the support element and to the treatment unit so as to create the necessary lines for blood circulation, discharge, infusion of possible substitution liquids, dialysis. Note that the connection of the distribution circuit to the treatment unit can be before, simultaneous to or follow the stage in which the circuitry is fastened to the support element. The stage in which the treatment unit is fastened to the support element comprises sub-stages in which a pair of connectors to which the counter-connectors 9, 10 housed by the blood treatment unit are to be fastened are chosen, in which a given amount of glue, normally based on a polymer resin, is placed in the ring-shaped seats 21 of each connector chosen, in which each counter-connector is at least partially fitted into its respective ring-shaped seat so as to obtain a mechanical blocking and a liquid-sealing coupling. Note that during said fitting stage at least a portion of the glue placed in the ring-shaped seat reaches the second zone 23 of said ring-shaped seat. At the end of said stage in which the counter-connector is fitted into its respective ring-shaped seat, the volume of glue previously placed plus the volume of the portion of counter-connector housed within the ring-shaped seat is smaller than the total volume of said ring-shaped seat. It is thus avoided that glue migrates towards the tubular channel 16 causing its partial or total occlusion.

The stage in which a fluid distribution circuit 15 is associated to the support element 4 and to the treatment unit 5 comprises in its turn the sub-stages in which an end portion of a discharge line 45 for a waste fluid is fastened fluid-sealingly with the second end portion 14 of one of said connectors, and in which an end portion of an intake line 48 for fresh dialysis liquid is fastened sealingly with the second end portion of another of said connectors. Said stage of association of the distribution circuit also comprises the sealing fastening of an end portion of a blood suction branch 46 with the inlet port to the first chamber, and an end portion of a blood return line 47 with the exit port from said first chamber. The fastening of the various end portions referred to above can take place by gluing, by forcing or by hot coupling.

Figure 15:
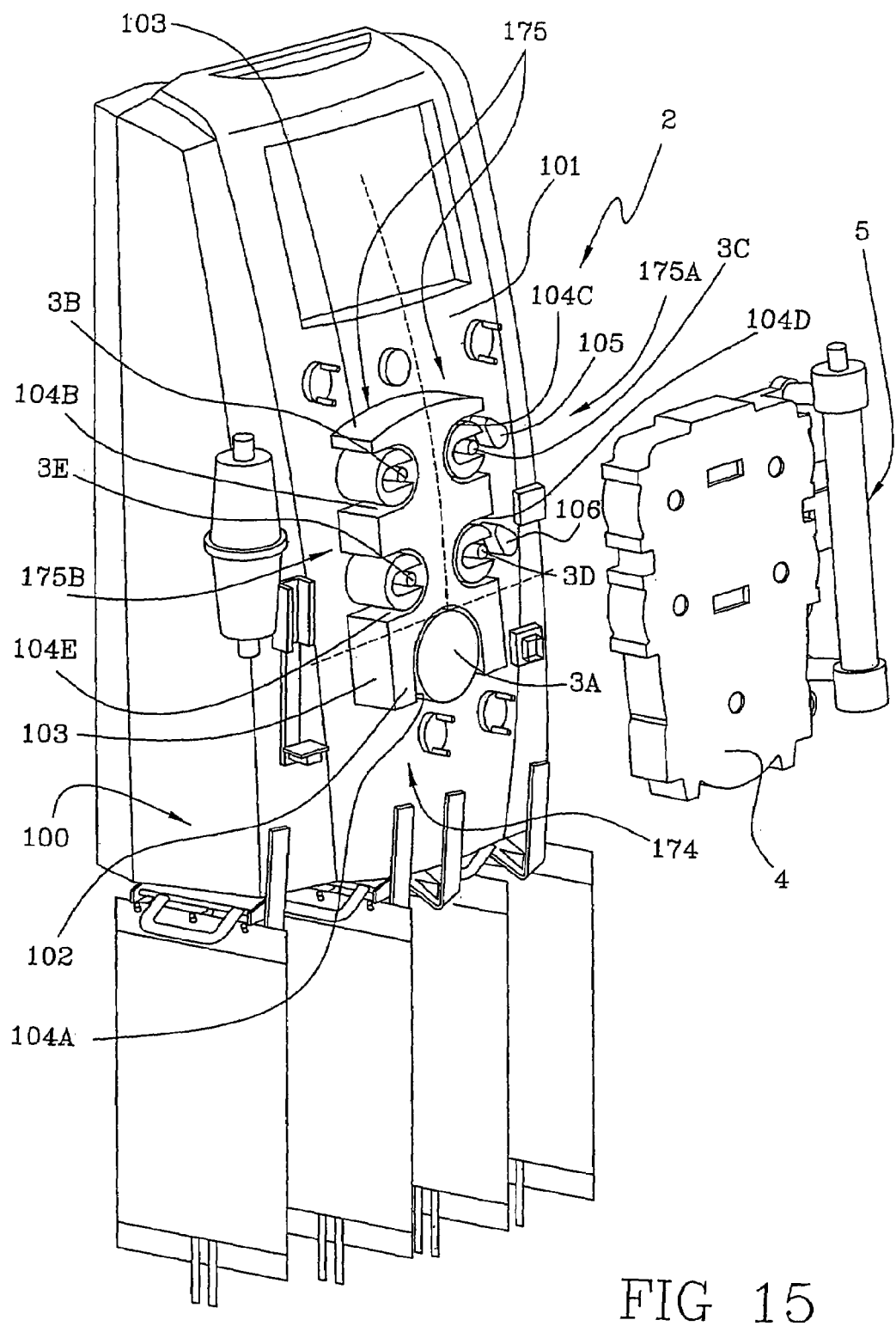
FIG. 15 shows an apparatus according to the present invention to which an integrated module can be associated.

Granted the above, it should be noted that the integrated module according to the present invention is designed to be used on an extracorporeal blood treatment apparatus 2 as shown in FIGS. 15 and 16.

In particular, said apparatus 2 comprises a body 100 provided on its front surface 101 with a given number of peristaltic pumps 3a, 3b, 3c, 3d, 3e designed to cooperate with the respective U-shaped tube lengths defined on the integrated module.

As can be noted from FIG. 15, the apparatus body 11 has a guiding and positioning projection 102 protruding from the surface 101, which is exactly counter-shaped to the peripheral wall 32 of the support element to which it should be coupled.

In other words, the guiding and positioning projection 102 has a side surface 103 which, when engaged to the integrated module, is delimited by the peripheral wall 32.

Also the peristaltic pumps protrude from the surface 101 of the apparatus body 100 and at least a part of their side surface is counter-shaped to the peripheral wall 32 of the support element.

In particular, it is exactly the curved portions defined by the curved lengths of the front wall 25 which are designed to couple with the protruding side portions of the pumps 3.

The protruding peristaltic pumps and the guiding and positioning projection 102 define together suitable seats 104*a*, 104*b*, 104*c*, 104*d* and 104*e* taking a basically semicircular or U shape and designed to receive the corresponding U-shaped tube lengths 44*a*, 45*a*, 48*a*, 50*a*, 51*a*.

Analogously to what has been described for the integrated module 1, also on the front wall of the apparatus a given number of zones can be defined, and in particular two zones 174, 175 in which the first zone 174 comprises the blood pump 3*a*, whereas the second zone 175 comprises the other pumps 3*b*, 3*c*, 3*d* and 3*e*.

The second zone 175 comprises at least two half-parts placed side by side 175*a*, 175*b*; the intake pump 3*c* and the infusion pump 3*d* are placed in said first half-part whereas the auxiliary pre-infusion pump 3*e* and the suction pump 3*b* are placed in the second half-part.

Here again the first and second half-part are specularly symmetrical and placed side by side on the front wall of the apparatus and above the first zone 174.

Eventually, it should be noted that there is at least a first moving element 105 and a second moving element 106 that are substantially identical and housed directly by the apparatus body; the latter are designed to act respectively on the infusion branch 77 and/or on the intake branch 76 (the first moving element), and on the pre-infusion branch 79 and/or on the post-infusion branch 80 (the second moving element 106). In particular, the selecting means 97 and 203 previously described can comprise said moving elements 105, 106 designed to be controlled by the CPU 209 so as to selectively determine the blocking or passage of fluid in either branch.

In order to cooperate with said moving elements the integrated module is equipped with the support structure with said infusion, intake, post-infusion and pre-infusion branches, which are all parallel to one another.

The invention has important advantages.

First of all, the present invention allows to obtain an integrated module for apparatus for extracorporeal blood treatment with an optimal arrangement of the various tube lengths of fluid lines.

The division of said module into two opposite zones allows to engage to one of the shorter sides a U-shaped tube length of a blood circuit with greater size than the U-shaped tube lengths of the other fluid lines, thus enabling the use of peristaltic pumps with greater size, which can allow higher flow rates and also, since longer tube lengths are used, less damages of the tube length on which the pump acts.

Moreover, the particular arrangement of the intake line for fresh dialysis liquid on the blood treatment element and on the post-infusion zone enables to minimize the length of the inlet portion of said intake line, thus minimizing the amount of fresh dialysis fluid to be wasted.

The same applies also to the pre-/post-infusion lines, which is also placed on the pre- and post-infusion zones and enables to minimize the lengths of the various branches.

It is evident that said positioning is extremely advantageous in intensive therapy apparatuss in which all biological fluids are contained in bags with limited volume.

Eventually, it should be pointed out that the presence of five peristaltic pumps on the apparatus and of corresponding U-shaped tube lengths on the integrated module enables the use of another line, in particular of a pre-infusion line, so as to allow the introduction, for instance, of topical anticoagulants without limiting pre- and post-infusion possibilities.

Finally, the use of a particular support element that is open on one side and defines a basically box-shaped body enables an optimal protection of the tube lengths of the respective peristaltic pumps when the unit is operating.

The invention claimed is:

1. An integrated fluid treatment module comprising:
a support element having a main body having:
two first opposite sides and two second opposite sides, said two second opposite sides being shorter than said two first opposite sides, and
at least one peripheral wall protecting away from said two second opposite sides;
fluid distribution circuitry associated to the support element and comprising:
at least a blood line, at least a portion of said blood line being fastened to one of said two second opposite sides of the support element and defining at least a U-shaped tube length with respect to said support element, said U-shaped tube length being designed to cooperate with a respective pump and extending inside the at least one peripheral wall of the support element; and
further fluid lines secured to at least one of said two first opposite sides of the support element, each of said further fluid lines defining at least a U-shaped tube length with respect to said support element, each said U-shaped tube length being designed to cooperate with a respective pump and extending inside the at least one peripheral wall of the support element, said U-shaped tube length of the blood line being longer and having a radius of curvature greater than the tube lengths defined by said further fluid lines;
the support element having a first zone to which the U-shaped tube length of the blood line is fastened, and at least a second zone opposite said first zone to which the U-shaped tube lengths of the further fluid lines are all fastened, said second zone comprising a first half-part and a second half part reciprocally placed side by side and being symmetrical along a longitudinal axis of the main body, the further fluid lines including two fluid lines connected to said first half-part and two fluid lines connected to said second half-part.

2. A module according to claim 1, wherein the further fluid lines comprise at least a discharge line for a waste fluid defining at least a tube length arranged as a U with respect to said support element and fastened to said second half-part.

3. A module according to claim 1, wherein the further fluid lines comprise at least an in-take line for fresh dialysis liquid, said in-take line defining at least a tube length arranged as a U with respect to said support element fastened to said first half-part.

4. A module according to claim 1, wherein said further fluid lines further comprise at least a fluid infusion line defining at least a tube length arranged as a U with respect to said support element and fastened to said first half-part.

5. A module according to claim 1, wherein said further fluid lines further comprise at least an auxiliary pre-infusion line defining at least a tube length arranged as a U with respect to said support element and fastened to said second half-part.

6. A module according to claim 1, wherein the support element further comprises a main body having a front wall delimited by said two first and two second opposite sides, said front wall and said at least one peripheral wall defining a housing compartment.

7. A module according to claim 6, wherein said two first opposite sides and said two second opposite sides are substantially parallel and reciprocally facing.

8. A module according to claim 7, wherein said two first opposite sides have a substantially rectilinear development, each of said two first opposite sides having two curved portions, said two curved portions on at least one of said first opposite sides having a cavity facing the other of said first opposite sides, and
said two second opposite sides have a substantially rectilinear development, at least one of said two second opposite sides having a curved portion positioned between two rectilinear lengths, said curved portion having a cavity facing the other of said two second opposite sides.

9. A module according to claim 8, wherein the first zone is partly delimited by at least one of said two second opposite sides having the curved portion and by a portion of one of said two first opposite sides beside the at least one of said two second opposite sides having the curved portion.

10. A module according to claim 8, wherein the second zone is partly delimited by one of said two second opposite sides without the curved portion and by a portion of said first opposite sides beside said second opposite side without the curved portion.

11. A module according to claim 1, wherein, when the module is associated to an extracorporeal blood treatment apparatus, the first zone of the support element is placed below the second zone of the support element.

12. A module according to claim 1, wherein, when the module is associated to an extracorporeal blood treatment apparatus, the first and second half-part of the second zone of the support element are placed side by side.

13. A module according to claim 8, wherein the U-shaped tube length of the blood line is fastened to the at least one of said two second opposite sides having the curved portion.

14. A module according to claim 3 wherein the tube length of the intake line for fresh dialysis liquid is fastened to one of said two first opposite sides.

15. A module according to claim 2 wherein the tube length of the discharge line for a waste fluid is fastened to one of said two first opposite sides.

16. A module according to claim 4 wherein the tube length of the fluid infusion line is fastened to one of said two first opposite sides.

17. A module according to claim 5 wherein the tube length of the auxiliary pre-infusion line is fastened to one of said two first opposite sides.

18. A module according to claim 1, wherein a length of every U-shaped tube portion is smaller than or the same as ($\pi R+2R$), where R is a respective radius of curvature of the U-shaped tube length.

19. A module according to claim 8, further comprising a support structure associated to the main body and placed laterally with respect to the main body.

20. A module according to claim 19, wherein said support structure is connected to the main body on one of said two first opposite sides.

21. A module according to claim 20, wherein the support structure is connected to the main body on said curved portions of one of said two first opposite sides.

22. A module according to claim 1, further comprising at least a blood treatment unit connected to the support element.

23. A module according to claim 7, wherein said support element comprises at least a first connector and a second connector connected to the main body, said first and second connectors being spaced away one from each other, said first and second connectors being configured to receive one or more corresponding counter-connectors of a blood treatment unit to be mounted onto the support element.

24. A module according to claim 23, further comprising a blood treatment unit connected to the support element, said blood treatment unit comprising:
a housing body;
at least a semipermeable membrane operating inside the housing body defining a first chamber and a second chamber;
a first counter-connector and a second counter-connector associated to the housing body and fastened to the respective first and second connectors associated to the main body, at least one of said first and second counter-connectors being in fluid communication with the second chamber of the treatment unit and with respective first end portions of said connectors;
at least an access port to said first chamber; and
at least an exit port from said first chamber.

25. A module according to claim 23, further comprising a support structure associated to the main body and placed laterally with respect to the main body, the first and second connectors and the support structure being positioned laterally with respect to the main body on one of said two first opposite sides.

26. A module according to claim 1, wherein the first half-part and the second half-part are specularly symmetrical with respect to a longitudinal axis of the main body.

27. An integrated fluid treatment module comprising:
a support element including:
a front wall having two first opposite sides and two second opposite sides,
the two first opposite sides being substantially parallel and reciprocally facing, said two first opposite sides having a substantially rectilinear development, each of said two first opposite sides having two curved portions, wherein cavities formed by each of said two curved portions on one of said two first opposite sides face the other of said two first opposite sides; and
the two second opposite sides being substantially parallel and reciprocally facing, said two second opposite sides having a substantially rectilinear development, at least one of said two second opposite sides having a curved portion placed between two rectilinear lengths, a cavity formed by said curved portion on one of said two second opposite sides facing the other of said two second opposite sides, at least a peripheral wall projecting away from said two second opposite sides;
fluid distribution circuitry associated to the support element and comprising:
at least one blood line, at least a portion of said at least one blood line being fastened to the peripheral wall of the support element corresponding to the curved portion of one of said two second opposite sides, said at least one blood line defining at least one U-shaped tube length with respect to said support element, said at least one U-shaped tube length being configured to cooperate with a respective pump and to extend inside the peripheral wall of the support element; and
further fluid lines secured to the peripheral wall of the support element corresponding to the curved portions of said two first opposite sides, each of said further fluid lines defining at least one U-shaped tube length with respect to said support element, each of said at least one U-shaped tube length being configured to cooperate with a respective pump and to extend inside the peripheral wall of the support element.

28. A module according to claim 27, wherein said support element has first zone to which the U-shaped tube length of the blood line is fastened, and at least a second zone opposite said first zone to which the U-shaped tube lengths of the further fluid lines are fastened.

29. A module according to claim 28, wherein said second zone comprises a first half-part and a second half-part reciprocally placed side by side, said first and second half-parts being symmetrical to a longitudinal axis of the main body, the further fluid lines being fastened on said second zone including at least two fluid lines connected to said first half-part and at least two fluid lines connected to said second half-part.

30. An apparatus for extracorporeal blood treatment comprising:
   a body, a number of pumps provided on a surface of the body, the number of pumps being designed to cooperate with a suitable fluid distribution circuitry to be associated to the apparatus, at least one of said number of pumps being a blood pump designed to cooperate with a respective blood line of the distribution circuitry, wherein the surface of the body has a first zone having said blood pump and at least a second zone, opposite said first zone, having the other of said number of pumps; and
   an integrated fluid treatment module according to claim 27 having the U-shaped tube lengths of the blood line and of the further fluid lines secured and cooperating with the number of pumps of said apparatus.

31. An apparatus according to claim 30, wherein said blood pump and the other of said number of pumps are peristaltic pumps, each comprising a moving arm rotating around a fulcrum, and an active element fastened to the moving arm, said active element operating on at least a deformable tube length associated with the peristaltic pump, the moving arm of the blood pump being longer than that of the other of said number of pumps.

32. An apparatus for extracorporeal blood treatment comprising:
   a body, a number of pumps provided on a surface of the body, the number of pumps being designed to cooperate with a suitable fluid distribution circuitry to be associated to the apparatus, at least one of said number of pumps being a blood pump designed to cooperate with a respective blood line of the distribution circuitry, wherein the surface of the body has a first zone having said blood pump and at least a second zone, opposite said first zone, having the other of said number of pumps; and
   an integrated fluid treatment module according to claim 22 having the U-shaped tube lengths of the blood line and of the further fluid lines secured and cooperating with the number of pumps of said apparatus.

33. An apparatus according to claim 32, wherein said blood pump and the other of said number of pumps are peristaltic pumps, each comprising a moving arm rotating around a fulcrum, and an active element fastened to the moving arm, said active element operating on at least a deformable tube length associated with the peristaltic pump, the moving arm of the blood pump being longer than that of the other of said number of pumps.

* * * * *

UNITED STATES PATENT AND TRADEMARK OFFICE
CERTIFICATE OF CORRECTION

PATENT NO. : 7,223,336 B2
APPLICATION NO. : 10/771427
DATED : May 29, 2007
INVENTOR(S) : Tonelli et al.

It is certified that error appears in the above-identified patent and that said Letters Patent is hereby corrected as shown below:

Column 18, line 16, "protecting" should read --projecting--.

Column 18, line 43, "second half part" should read --second half-part--.

Column 19, line 40, "claim 3 wherein" should read --claim 3, wherein--.

Column 19, line 43, "claim 2 wherein" should read --claim 2, wherein--.

Column 19, line 46, "claim 4 wherein" should read --claim 4, wherein--.

Column 19, line 49, "claim 5 wherein" should read --claim 5, wherein--.

Column 21, line 6, "has first zone" should read --has a first zone--.

Signed and Sealed this

Seventh Day of August, 2007

JON W. DUDAS
*Director of the United States Patent and Trademark Office*